U S008207181B2

United States Patent
Kosley, Jr. et al.

(10) Patent No.: US 8,207,181 B2
(45) Date of Patent: Jun. 26, 2012

(54) SUBSTITUTED DIHYDRO, TRIHYDRO AND TETRAHYDRO CYCLOALKYLOXAZOLOPYRIMIDINONES, PREPARATION AND USE THEREOF

(75) Inventors: Raymond Walter Kosley, Jr., Bridgewater, NJ (US); Rosy Sher, Bridgewater, NJ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/875,700

(22) Filed: Sep. 3, 2010

(65) Prior Publication Data

US 2011/0077257 A1 Mar. 31, 2011

Related U.S. Application Data

(63) Continuation of application No. PCT/US2008/056009, filed on Mar. 6, 2008.

(51) Int. Cl.
*A01N 43/54* (2006.01)
*A61K 31/505* (2006.01)
*C07D 239/00* (2006.01)

(52) U.S. Cl. ...................... 514/267; 544/250
(58) Field of Classification Search .................. 514/267, 514/250
See application file for complete search history.

(56) References Cited

FOREIGN PATENT DOCUMENTS

| WO | WO 2006/030032 | 3/2006 |
| WO | WO 2006/084634 | 8/2006 |
| WO | WO 2008/112483 | 9/2008 |

OTHER PUBLICATIONS

Adetchessi, et al., Synthesis and Rearrangement of Cycloalkyl[1,2-e]oxazolo[3,2-a]pyrimidin-8/9-ones: An Access to Cycloalkyl[1,2-d]oxazolo[3,2-a]pyrimidin-5-ones, Tetrahedron, 61(18), 4453-4460 (2005).*
Watkins, J. C., et. al., Excitatory Amino Acid Transmitters, Ann. Rev. Pharmacol. Toxicol., (1981), vol. 21, pp. 165-204.
Adetchessi, O-S., et. al., Synthesis and Rearrangement of Cycloalkyl[1,2-e]Oxazolo[3,2-a] Pyrimidin-8/9-Ones: An Access to Cycloalkyl[1,2-d]Oxazolo[3,2-a]Pyrimidin-5-Ones, Tetrahedron, vol. 61, (2005). pp. 4453-4460.
Alexander, G. M., et. al., Metabotropic Glutamate Receptors as a Strategic Target for the Treatment of Epilepsy, Epilepsy Research, vol. 71, pp. 1-22, (2006).
Borsini, F., et. al., A Model to Measure Anticipatory Anxiety in Mice?, Psychopharmacology, (1989), vol. 98, pp. 207-211.
Chavez-Noriega, L. E., et. al., Metabotropic Glutamate Receptors: Potential Drug Targets for the Treatment of Schizophrenia, Current Drug Targets,—CNS & Neurological Disorders, (2002), vol. 1, pp. 261-281.
Feinberg, I., et. al., The Selective Group Mglu2/3 Receptor Agonist Ly379268 Suppresses Rem Sleep and Fast EEG in the Rat, Pharmacology, Biochemistry and Behavior, vol. 73, (2002), pp. 467-474.
Forfar, I., et. al., An easy Route to 2-Substituted-2,3-Dihydro-5(7)H-Oxazolo[3,2-a]Pyrimidin-5-ones and 7-ones Starting from the Corresponding 2-Amino-2-Oxazolines, Journal of Heterocyclic Chemistry, (2001), vol. 38, No. 4, pp. 823-827.
Forfar, I., et. al., Synthesis, Structure, and Preliminary Pharmacological Evaluation of Cycloaddition Compounds with Unsaturated Carboxlic Esters, Archie der Pharmazie, (1990), vol. 323, No. 11, pp. 905-909.
Galici, R., et. al., Biphenyl-Indanone A, A Positive Allosteric Modulator of the Metabotropic Glutamate Receptor Subtype 2, Has Antipsychotic- and Anxiolytic-Like Effects in Mice, The Journal of Pharmacology and Experimental Therapeutics, (2006), vol. 318, No. 1, pp. 173-185.
Gewirtz, J. C., et, al., Modulation of DOI-Induced Increases in Cortical BDNF Expression by Group II mGlu Receptors, Pharmacology, Biochemistry and Behaviour, vol. 73, (2002), pp. 317-326.
Helton, D. R., et. al., Anxiolytic and Side-Effect Profile of Ly354740: A Potent, Highly Selective, Orally Active Agonist for Group II Metabotropic Glutamate Receptors, The Journal of Pharmacology and Experimental Therapeutics, vol. 284, No. 2, pp. 651-660, (1998).
Johnson et al, Metabotropic glutamate 2 receptor potentiators: receptor modulation, frequency-dependent synaptic activity, and efficacy in preclinical anxiety and psychosis model(s), Psychopharmacology (2005) 179 pp. 271-283.
Jones, C. K., et. al. , Analgesic Effects of the Selective Group II (mGlu2/3) Metabotropic Glutamate Receptor Agonists Ly379268 and Ly389795 in Persistent and Inflammatory Pain Models after Acute and Repeated Dosing, Neuropharmacology, vol. 49, (2005), pp. 206-218.

(Continued)

*Primary Examiner* — Andrew D Kosar
*Assistant Examiner* — Erich A Leeser
(74) *Attorney, Agent, or Firm* — Kelly L. Bender

(57) ABSTRACT

The present disclosure relates to a series of 2-substituted-di-tri or tetra-hydro-8H-cyclopentaoxazolo[3,2-a]pyrimidin-8-ones and 2-substituted-di-, tetra-, or hexa-hydro-cyclohexaoxazolo[3,2-a]pyrimidin-9-ones of formula (I):

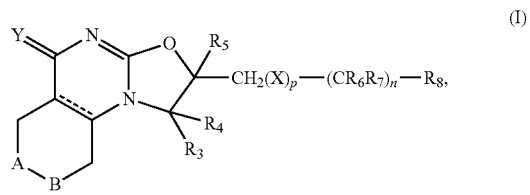

wherein p, n, A, B, X, Y, $R_1$, $R_2$, $R_3$, $R_4$, $R_5$, $R_6$, $R_7$ and $R_8$ are as defined herein. This invention also relates to methods of making these compounds including novel intermediates. The compounds of this invention are modulators of metabotropic glutamate receptors (mGluR), particularly, mGluR2 receptor. Therefore, the compounds of this invention are useful as pharmaceutical agents, especially in the treatment and/or prevention of a variety of central nervous system disorders (CNS), including but not limited to acute and chronic neurodegenerative conditions, psychoses, convulsions, anxiety, depression, migraine, pain, sleep disorders and emesis.

13 Claims, No Drawings

OTHER PUBLICATIONS

Kawashima, N., et. al., Neuropharmacological Profiles of Antagonists of Group II Metabotropic Glutamate Receptors, Neuroscience Letters, vol. 378, (2005), pp. 131-134.

Kellner et al, Effects of a metabotropic glutamate2/3 receptor agonist (LY544344/LY354740) on panic anxiety induced by cholecystokinin tetrapeptide in healthy humans: preliminary results, Psychopharmacology (2005) 179 pp. 310-315.

Krystal et al, Preliminary evidence of attenuation of the disruptive effects of the NMDA glutamate receptor antagonist, ketamine, on working memory by pretreatment with the group II metabotropic glutamate receptor agonist, LY354740, in healthy human subjects, Psychopharmacology (2005) 179 pp. 303-309.

Monaghan, D. T., et. al., The Excitatory Amino Acid Receptors: Their Clases, Pharmacology, and Distinct Properties in the Funchtion of the Central Nervous System, Annu. Rev, Pharmacol. Toxicol., (1989), vol. 29, pp. 365-402.

Olivier, B., et. al., Stress-Induced Hyperthermia and Anxiety: Pharmacological Validation, European Journal of Pharmacology, vol. 463, (2003), pp. 117-132.

Patil, S. T., et. al., Activation of MGlu2/3 Receptors as a New Approach to Treat Schizophrenia: A Randonmized Phase 2 Clinical Trial, Nature Medicine, vol. 13, No. 9, (2007), pp. 1102-1107.

Rorick-Kehn, L., et. al., Improved Bioavailability of the MGlu2/3 Receptor Agonist Ly354740 Using a Prodrug Strategy: In Vivo Pharmacology of Ly54434, The Journal of Pharmacology and Experimental Therapeutics, (2006), vol. 316, No. 2, pp. 905-913.

Sabbatini, F. M., et. al., Metabotropic Glutamate Receptors: Potential Therapeutic Applications of Recently Disclosed New Chemical Entities, Expert Opin. Ther. Patents, (2004), vol. 14, No. 11, pp. 1593-1604.

Schechter, L. E., et. al., Innovative Approaches for the Developement of Antidepressant Drugs: Current and Future Strategies, NeuroRx: The Journal of the American Society for Experimental NeuroTherapeutics, vol. 2, pp. 590-611, (2005).

Tatarczynska et al, The antianxiety-like effects of antagonists of group I and agonists of group II and III metabotropic glutamate receptors after intrahippocampal administration, Psychopharmacology (2001) 158 pp. 94-99.

Thomsen, C., et. al., (S)-4-Carboxy-3-Hydroxyphenylglycine, An Antagonist of Metabotropic Glutamate Receptor (MGluR)1a and an Agonist of MGluR2, Protects Against Audiogenic Seizures in DBA/2 Mice, Journal of Neurochemistry, vol. 62, No. 6, pp. 2492-2495, (1994).

Thomsen, C., et. al., Roles of Metabotropic Glutamate Receptor Subtypes in Modulation of Pentylenetetrazole-Induced Seizure Activity in Mice, Neuropharmacology, vol. 37, (1998), pp. 1465-1473.

Watkins et al, Structure-activity relationships in the development of excitatory amino acid receptor agonists and competitive antagonists, Trends in Pharma. Sci. (1990) 11 pp. 25-33.

International Search Report for WO2009/110901 dated Sep. 11, 2009.

* cited by examiner

SUBSTITUTED DIHYDRO, TRIHYDRO AND TETRAHYDRO CYCLOALKYLOXAZOLOPYRIMIDINONES, PREPARATION AND USE THEREOF

This application is a continuation of International Application No. PCT/US2008/056009, filed Mar. 6, 2008, which is incorporated herein by reference in its entirety

BACKGROUND OF THE INVENTION

1. Field of the Invention

The present invention relates to a series of substituted dihydro, trihydro and tetrahydro cycloalkyloxazolopyrimidinones. More specifically, the present invention relates to a series of 2-substituted-di- tri or tetra-hydro-8H-cyclopentaoxazolo[3,2-a]pyrimidin-8-ones and 2-substituted-di-, tetra-, or hexa-hydro-cyclohexaoxazolo[3,2-a]pyrimidin-9-ones. This invention also relates to methods of making these compounds. The compounds of this invention are allosteric modulators of metabotropic glutamate receptors (mGluR), particularly, mGluR2. Therefore, the compounds of this invention are useful as pharmaceutical agents, especially in the treatment and/or prevention of a variety of diseases including diseases associated with the central nervous system.

2. Description of the Art

Recently, there has been a considerable amount of research involving L-glutamate, which is the most abundant neurotransmitter in the central nervous system (CNS). More specifically, L-glutamate mediates the major excitatory pathways in mammals, and is therefore referred to as an excitatory amino acid (EAA). Thus the receptors that respond to glutamate are known as excitatory amino acid receptors (EAA receptors). Based on the extensive research performed lately it can be readily discerned that EAAs are of great physiological importance. Particularly, EAAs are known to play a role in several physiological processes including long-term potentiation (learning and memory), the development of synaptic plasticity, motor control, respiration, cardiovascular regulation and sensory perception, just to name a few. See, e.g., Watkins & Evans, Annual Reviews in Pharmacology and Toxicology, 21:165 (1981); Monaghan, Bridges, and Coltman, Annual Reviews in Pharmacology and Toxicology, 29:365 (1989); Watkins, Krogsgaard-Larsen and Honore, Transactions in Pharmaceutical Science, 11:25 (1990).

Broadly, the EAA receptors are classified into two types: 1) "ionotropic"—which are directly coupled to the opening of cation channels in the cell membrane of the neurons; and 2) "metabotropic"—which are G-protein coupled receptors (GPCR). The excessive or inappropriate stimulation of EAA receptors leads to neuronal cell damage or loss by way of a mechanism known as excitotoxicity. This process has been suggested to mediate neuronal degeneration in a variety of conditions. Thus there is a renewed interest in developing small molecule new drugs to alleviate these conditions.

The metabotropic glutamate receptors (mGluR) are a highly heterogeneous family of glutamate receptors that are linked to multiple second-messenger pathways. One function of these receptors is to modulate the presynaptic release of glutamate and the postsynaptic sensitivity of the neuronal cell to glutamate excitation. Thus it has been reported widely in the literature that agonists and antagonists of these receptors are useful in the treatment of a variety of disease conditions including acute and chronic neurodegenerative conditions, psychoses, convulsions, anxiety, depression, migraine, pain, sleep disorders and emesis.

The metabotropic glutamate receptors (mGluR) are again classified into three groups based on receptor homology and signaling mechanisms. Among them, recent pharmacological and histochemical studies have suggested that the group II mGluR (mGluR2 and mGluR3) plays crucial roles in the control of emotional states. For example, MGS0039, a selective group II mGluR antagonist, has been shown to exhibit dose-dependent antidepressant-like effects in some animal models. See, e.g., Kawashima, et al., Neurosci. Lett., 2005, 378(3):131-4.

Recently, it has also been reported that glutamate/N-methyl-D-aspartate glutamate receptors (NMDAR) are implicated in schizophrenia. This was indeed supported by the observation that administration of NMDAR blockers to human volunteers is psychotomimetic and administration to schizophrenia patients exacerbates pre-existing symptoms. For example, systemic administration of group II mGluR agonists suppress phencyclidine (PCP) induced behavioral effects and the increase in glutamate efflux. It has also been observed that activation of group II mGluRs (mGluR2 and mGluR3) decreases glutamate release from presynaptic nerve terminals, suggesting that group II mGluR agonists may be beneficial in the treatment of schizophrenia. See, e.g., Chavez-Noriega et al., Current Drug Targets—CNS & Neurological Disorders, 2002, 1, 261-281.

Although there is a great deal of interest in developing small molecule drugs that are active at the mGluR sites, the researchers are faced with a lack of potent and selective molecules. In spite of this, there are innumerable reports highlighting the great interest around these potential therapeutic targets. See, e.g., Sabbatini and Micheli, Expert Opin. Ther. Patents (2004) 14(11):1593-1604.

However, there is still a need to develop selective compounds for one subtype over another metabotropic glutamate receptor site. One strategy that has recently emerged involves the discovery of allosteric modulators that do not bind at the glutamate binding site. An allosteric modulator only works if the agonist (glutamate) is present at the orthosteric binding site; thus, an allosteric modulator will only potentiate or block effects produced by the presence of an agonist, but have no activity on its own. Such a strategy is believed to confer greater specificity to desired pharmacological effects because they affect the normal physiological activity of the agonist.

In addition, there is still a considerable interest in developing small molecule "drug like" compounds that exhibit improved potency and modulation of mGluR2 as well as improved brain penetration. There is also an interest in developing modulators of mGluR2 that are devoid of typical side effects exhibited by typical and atypical antipsychotic compounds, such as for example extrapyramidal symptoms including tardive dyskinesia, weight gain, etc. It is also expected that allosteric modulators that exhibit improved subtype selectivity will feature an improved pharmacological safety profile. It is further believed that a selective modulator of mGluR2 will also exhibit efficacy on cognitive dysfunction in schizophrenia patients thereby improving working memory and positive symptoms.

All of the references described herein are incorporated herein by reference in their entirety.

Accordingly, it is an object of this invention to provide a series of 2-substituted-di- tri or tetra-hydro-8H-cyclopentaoxazolo[3,2-a]pyrimidin-8-ones and 2-substituted-di-, tetra-, or hexa-hydro-cyclohexaoxazolo[3,2-a]pyrimidin-9-ones which are potent modulators of mGluR2.

It is also an object of this invention to provide processes for the preparation of the substituted dihydro and tetrahydro oxazolopyrimidinones as disclosed herein.

Other objects and further scope of the applicability of the present invention will become apparent from the detailed description that follows.

SUMMARY OF THE INVENTION

Thus in accordance of this invention there are provided compounds of the formula I:

$$\text{(I)}$$

(structure showing a bicyclic system with Y=, N, O, $R_5$, $CH_2(X)_p$—$(CR_6R_7)_n$—$R_8$, $R_4$, $R_3$, A, B)

wherein:
----- is a single or a double bond;
p is 0 or 1;
n is an integer from 0 to 3;
X is oxygen, sulfur or $NR_{21}$, wherein $R_{21}$ is hydrogen or $(C_1-C_4)$alkyl;
Y is oxygen or sulfur;
A is a single covalent bond or $CHR_1$;
B is $CHR_2$, $NR_2$, oxygen or sulfur;
$R_1$ and $R_2$ are the same or different and independently of each other selected from the group consisting of hydrogen, $CF_3$, straight or branched chain $(C_1-C_{10})$alkyl, mono- or di-fluoro$(C_1-C_4)$alkyl, mono- or di-fluoro$(C_1-C_4)$alkoxy$(C_0-C_4)$alkyl, mono- or di-fluoro$(C_1-C_4)$alkylsulfanyl$(C_0-C_4)$alkyl, mono- or di-fluoro$(C_1-C_4)$alkylsulfinyl$(C_0-C_4)$alkyl, mono- or di-fluoro$(C_1-C_4)$alkylsulfonyl$(C_0-C_4)$alkyl, $(C_1-C_{10})$alkoxy$(C_0-C_4)$alkyl, $(C_1-C_{10})$alkylsulfanyl$(C_0-C_4)$alkyl, $(C_1-C_{10})$alkylsulfinyl$(C_0-C_4)$alkyl, $(C_1-C_{10})$alkylsulfonyl$(C_0-C_4)$alkyl, $(C_1-C_{10})$alkoxy mono- or di-fluoro$(C_1-C_4)$alkyl, $(C_1-C_{10})$alkylsulfanyl mono- or di-fluoro$(C_1-C_4)$alkyl, $(C_1-C_{10})$alkylsulfinyl mono- or di-fluoro$(C_1-C_4)$alkyl, $(C_1-C_{10})$alkylsulfonyl mono- or di-fluoro$(C_1-C_4)$alkyl, $(C_6,C_{10})$aryl$(C_0-C_4)$alkyl, $(C_6,C_{10})$aryl mono- or difluoro$(C_1-C_4)$alkyl, $(C_6,C_{10})$aryl mono- or difluoro$(C_2-C_4)$alkyloxy, $(C_6,C_{10})$aryloxy$(C_0-C_4)$alkyl, $(C_6,C_{10})$arylsulfanyl$(C_0-C_4)$alkyl, $(C_6,C_{10})$arylsulfinyl$(C_0-C_4)$alkyl, $(C_6,C_{10})$arylsulfonyl$(C_0-C_4)$alkyl, $(C_3-C_8)$cycloalkyl$(C_0-C_4)$alkyl, mono- or difluoro$(C_3-C_8)$cycloalkyl$(C_0-C_4)$alkyl, $(C_3-C_8)$cycloalkoxy$(C_0-C_4)$alkyl, mono- or difluoro$(C_3-C_8)$cycloalkyloxy$(C_0-C_4)$alkyl, $(C_3-C_8)$cycloalkyl mono- or difluoro$(C_1-C_4)$alkyl, $(C_3-C_8)$cycloalkyl mono- or difluoro$(C_2-C_4)$alkyloxy, $(C_3-C_8)$cycloalkylsulfanyl$(C_0-C_4)$alkyl, $(C_3-C_8)$cycloalkylsulfinyl$(C_0-C_4)$alkyl, $(C_3-C_8)$cycloalkylsulfonyl$(C_0-C_4)$alkyl, hydroxy$(C_1-C_4)$alkyl, heteroaryl$(C_0-C_4)$alkyl, heteroaryl mono- or difluoro$(C_1-C_4)$alkyl, heteroaryloxy$(C_0-C_4)$alkyl, heteroaryloxy mono- or difluoro$(C_2-C_4)$alkyl, heteroarylsulfanyl$(C_0-C_4)$alkyl, heteroarylsulfinyl$(C_0-C_4)$alkyl, heteroarylsulfonyl$(C_0-C_4)$alkyl, saturated heterocyclic$(C_0-C_4)$alkyl, saturated heterocyclic mono- or di-fluoro$(C_1-C_4)$alkyl, saturated heterocyclyloxy$(C_0-C_4)$alkyl, saturated heterocyclyloxy mono- or di-fluoro$(C_2-C_4)$alkyl, saturated heterocyclylsulfanyl$(C_0-C_4)$alkyl, heterocyclylsulfinyl$(C_0-C_4)$alkyl, heterocyclylsulfonyl$(C_0-C_4)$alkyl, —$CO_2R_{22}$ or —$CONR_{23}R_{24}$ wherein $R_{22}$, $R_{23}$ and $R_{24}$ are the same or different and independently of each other selected from hydrogen or $(C_1-C_4)$alkyl; and wherein $R_1$ and $R_2$ are optionally further substituted;

$R_3$ and $R_4$ are the same or different and independently of each other selected from the group consisting of hydrogen, $(C_1-C_4)$alkyl, $(C_3-C_8)$cycloalkyl, and $(C_6,C_{10})$aryl $(C_1-C_4)$alkyl; or $R_3$ and $R_4$ taken together with the carbon atom to which they are attached form a substituted or unsubstituted $C_5-C_7$ carbocyclic ring;

$R_5$, $R_6$ and $R_7$ are the same or different and independently of each other selected from the group consisting of hydrogen, $(C_1-C_4)$alkyl and $(C_3-C_8)$cycloalkyl;

$R_8$ is selected from the group consisting of substituted or unsubstituted phenyl, substituted or unsubstituted naphthyl, substituted or unsubstituted indanyl, substituted or unsubstituted tetralinyl, substituted or unsubstituted benzocycloheptanyl, substituted or unsubstituted hexahydrofluorenyl, substituted or unsubstituted $(C_3-C_8)$cycloalkyl, substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, substituted or unsubstituted tetrahydrodibenzofuranyl and substituted or unsubstituted hexahydrodibenzofuranyl;

wherein said substituents are selected from the group consisting of $CF_3$, $OCF_3$, halogen, CN, $SF_5$, straight or branched chain $(C_1-C_{20})$alkyl, $(C_1-C_4)$alkylsulfonyl, substituted or unsubstituted $(C_3-C_{10})$cycloalkyl $(CR_9R_{10})_m$, substituted or unsubstituted $(C_6-C_{16})$spirocycloalkyl, substituted or unsubstituted $(C_6,C_{10})$aryl $(CR_9R_{10})_m$, substituted or unsubstituted heteroaryl $(CR_9R_{10})_m$, substituted or unsubstituted $(C_6,C_{10})$aryl $(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_3-C_{10})$cycloalkoxy, substituted or unsubstituted $(C_6,C_{10})$aryloxy, substituted or unsubstituted heteroaryloxy, substituted or unsubstituted piperidinyl$(CR_9R_{10})_m$, substituted or unsubstituted piperazinyl$(CR_9R_{10})_m$, substituted or unsubstituted $(C_4-C_7)$lactam, substituted or unsubstituted tetrahydropyranyl$(CR_9R_{10})_m$, substituted or unsubstituted tetrahydrofuranyl$(CR_9R_{10})_m$, substituted or unsubstituted 1,3-dioxanyl, substituted or unsubstituted 1,3-dioxolanyl, $(C_1-C_4)$alkoxyethoxy, substituted or unsubstituted $(C_3-C_8)$cycloalkyloxyethoxy, substituted or unsubstituted $(C_6,C_{10})$aryloxyethoxy and substituted or unsubstituted heteroaryloxyethoxy;

wherein m is an integer from 0 to 10;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ carbocyclic ring;

and wherein said substituents are selected from the aforementioned substituents.

The compound of formula I can be present as a salt. It can also present as an enantiomer, a stereoisomer or a tautomer or a racemic mixture thereof. All of these forms are part of this invention.

However, with the proviso that:
when ----- is a double bond, X and Y are oxygen, p is 1, n is 0, A is a single covalent bond or A is $CHR_1$, B is $CHR_2$, and wherein $R_1$, $R_2$, $R_3$, $R_4$ and $R_5$ are hydrogen, then $R_8$ is not phenyl or 4-ethylphenyl; and
when ----- is a double bond, X and Y are oxygen, p and n are 0, A is a single covalent bond or A is $CHR_1$, B is $CHR_2$, and wherein $R_1$, $R_2$, $R_3$, $R_4$ and $R_5$ are hydrogen, then $R_8$ is not piperidine.

More specifically, the following compounds are excluded from this invention:
5,6,7,8-tetrahydro-2-phenoxymethyl-9H-cyclohexa[1,2-e]oxazolo[3,2-a]pyrimidin-9-one;
5,6,7,8-tetrahydro-2-(4-ethylphenoxymethyl)-9H-cyclohexa[1,2-e]oxazolo[3,2-a]pyrimidin-9-one;
5,6,7,8-tetrahydro-2-(1-piperidinomethyl)-9H-cyclohexa[1,2-e]oxazolo[3,2-a]pyrimidin-9-one;
5,6,7-trihydro-2-phenoxymethyl-8H-cyclopenta[1,2-e]oxazolo[3,2-a]pyrimidin-8-one;
5,6,7-trihydro-2-(4-ethylphenoxymethyl)-8H-cyclopenta[1,2-e]oxazolo[3,2-a]pyrimidin-8-one; and
5,6,7-trihydro-2-(piperidinomethyl)-8H-cyclopenta[1,2-e]oxazolo[3,2-a]pyrimidin-8-one.

In addition, various embodiments of this invention including pharmaceutical compositions comprising various compounds of this invention as well as their use in the treatment of a variety of disorders and/or disease conditions as disclosed herein are also part of this invention all of which are described in detail below.

DETAILED DESCRIPTION OF THE INVENTION

The terms as used herein have the following meanings:
As used herein, the expression "$(C_1-C_4)$alkyl" includes methyl and ethyl groups, and straight-chained or branched propyl and butyl groups. Particular alkyl groups are methyl, ethyl, n-propyl, isopropyl and tert-butyl. Similarly, the expression "$(C_1-C_{10})$alkyl" includes all of the $(C_1-C_4)$alkyl as described above and further includes straight chained or branched pentyl, hexyl, heptyl, octyl, nonyl and decyl groups. Further, the expression "$(C_1-C_{20})$alkyl" includes all of the possible straight chained or branched alkyl groups containing from 1 to 20 carbon atoms. It should particularly be noted that any of the feasible branched $(C_1-C_4)$alkyl group, $(C_1-C_{10})$alkyl group or $(C_1-C_{20})$alkyl group known in the art is encompassed by this expression. Derived expressions such as "$(C_1-C_4)$alkoxy" or "$(C_1-C_{10})$alkoxy", "$(C_1-C_4)$thioalkyl" or "$(C_1-C_{10})$thioalkyl", "$(C_1-C_4)$alkoxy$(C_1-C_4)$alkyl" or "$(C_1-C_{10})$alkoxy$(C_1-C_{10})$alkyl", "hydroxy$(C_1-C_4)$alkyl" or "hydroxy$(C_1-C_{10})$alkyl", "$(C_1-C_4)$alkylcarbonyl" or "$(C_1-C_{10})$alkylcarbonyl", "$(C_1-C_4)$alkoxycarbonyl$(C_1-C_4)$alkyl", "$(C_1-C_4)$alkoxycarbonyl", "amino$(C_1-C_4)$alkyl", "$(C_1-C_4)$alkylamino", "$(C_1-C_4)$alkylcarbamoyl$(C_1-C_6)$alkyl", "$(C_1-C_4)$dialkylcarbamoyl$(C_1-C_4)$alkyl" "mono- or di-$(C_1-C_4)$alkylamino$(C_1-C_4)$alkyl", "amino$(C_1-C_4)$alkylcarbonyl" "diphenyl$(C_1-C_4)$alkyl", "phenyl$(C_1-C_4)$alkyl", "phenylcarboyl$(C_1-C_4)$alkyl", "phenoxy$(C_1-C_4)$alkyl" and "$(C_1-C_4)$alkylsulfonyl," are to be construed accordingly. Similarly other derived expressions, such as $(C_1-C_4)$alkoxyethoxy shall be construed accordingly. Another derived expression mono- or di-fluoro$(C_1-C_4)$alkyl shall mean that one or two of the hydrogens are replaced with fluorine. Representative examples of monofluoro$(C_1-C_4)$alkyl include fluoromethyl, 2-fluoro-eth-1-yl or 1-fluoro-eth-1-yl, 1-fluoro-1-methyl-eth-1-yl, 2-fluoro-1-methyl-eth-1-yl, 3-fluoro-prop-1-yl, and the like. Representative examples of difluoro$(C_1-C_4)$alkyl include difluoromethyl, 2,2-difluoro-eth-1-yl, 1,2-difluoro-eth-1-yl or 1,1-difluoro-eth-1-yl, 1,2-difluoro-1-methyl-eth-1-yl, 2,2-difluoro-1-methyl-eth-1-yl, 1,3-difluoro-prop-1-yl, and the like.

As used herein, the expression "$(C_3-C_8)$cycloalkyl" includes all of the known cyclic radicals. Representative examples of "cycloalkyl" includes without any limitation cyclopropyl, cyclobutyl, cyclopentyl, cyclohexyl, cycloheptyl, cyclooctyl, and the like. Derived expressions such as "cycloalkoxy" or "cycloalkyloxy", "cycloalkyloxyethoxy", "cycloalkylalkyl", "cycloalkylaryl", "cycloalkylcarbonyl" are to be construed accordingly. It should further be noted that the expression "$(C_5-C_8)$carbocyclic" shall have the same meaning as "$(C_5-C_8)$cycloalkyl".

As used herein the expression "$(C_1-C_6)$acyl" shall have the same meaning as "$(C_1-C_6)$alkanoyl", which can also be represented structurally as "R—CO—," where R is a $(C_1-C_5)$ alkyl as defined herein. Additionally, "$(C_1-C_5)$alkylcarbonyl" shall mean same as $(C_1-C_6)$acyl. Specifically, "$(C_1-C_6)$acyl" shall mean formyl, acetyl or ethanoyl, propanoyl, n-butanoyl, etc. Derived expressions such as "$(C_1-C_6)$acyloxy" and "$(C_1-C_6)$acyloxyalkyl" are to be construed accordingly.

As used herein, the expression "$(C_4-C_7)$lactam" represents all of the known $(C_4-C_7)$cyclic amide. Representative examples of "$(C_4-C_7)$lactam" includes azetidin-2-one, pyrrolidin-2-one, piperidin-2-one and azepan-2-one.

As used herein, the expression "$(C_1-C_6)$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$(C_1-C_6)$perfluoroalkoxy", is to be construed accordingly.

As used herein, the expression "mono- or difluoro$(C_1-C_4)$alkyl" means that any of the alkyl groups are substituted with one or two fluorine atoms. Such examples include, without any limitation, fluoromethyl, 1-fluoroethyl, 1-fluoropropyl, 1,1- or 1,2-difluoroethyl, 1,1-, 1,2- or 1,3-difluoropropyl, 1,1-, 1,2-, 1,3- or 1,4-difluorobutyl and so on. The derived expressions, "mono- or di-fluoro$(C_1-C_4)$alkoxy$(C_0-C_4)$alkyl, mono- or di-fluoro$(C_1-C_4)$alkylsulfanyl$(C_0-C_4)$alkyl, mono- or di-fluoro$(C_1-C_4)$alkylsulfinyl$(C_0-C_4)$-alkyl, mono- or di-fluoro$(C_1-C_4)$alkylsulfonyl$(C_0-C_4)$alkyl" shall be construed accordingly. However, in these situations, the placement of fluorine atom does become important. It is generally preferred that there is no fluorine atom on the carbon next to the oxygen, sulfur, sulfinyl or sulfonyl group. Thus, for instance, when the generic group is mono- or difluoroethoxymethyl, the preferred examples include only 2-fluoroethoxymethyl or 2,2-difluoroethoxymethyl, and the like.

As used herein mono- or difluoro$(C_3-C_8)$cycloalkyl shall mean one or two of the hydrogen atoms are replaced with fluorine atoms. Representative examples include fluorocyclohexyl, 1,2-, 2,2- or 1,3-difluorocyclohexyl, fluorocyclopentyl, 1,2-, 2,2- or 1,3-difluorocyclopentyl, and the like.

As used herein, the expression "$(C_6,C_{10})$aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expressions "$(C_6,C_{10})$aryloxy" and "$(C_6,C_{10})$aryloxyethoxy" shall be construed accordingly.

As used herein, the expression "$(C_6,C_{10})$aryl$(C_1-C_4)$alkyl" means that the $(C_6,C_{10})$aryl as defined herein is further attached to $(C_1-C_4)$alkyl as defined herein. Representative examples include benzyl, phenylethyl, 2-phenylpropyl, 1-naphthylmethyl, 2-naphthylmethyl and the like. Similarly, another derived expression "$(C_6,C_{10})$aryl$(C_3-C_8)$cycloalkyl" shall be construed accordingly. Representative examples of said expression include without any limitation, phenylcyclopropyl, 1-naphthylcyclopropyl, phenylcyclohexyl, 2-naphthylcyclopentyl, and the like.

As used herein, the expression "heteroaryl" includes all of the known heteroatom containing aromatic radicals. Representative 5-membered heteroaryl radicals include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, cinnolyl, benzimidazolyl, indazolyl, furopyridyl, thienopyridyl, and the like radicals. Derived expressions "heteroaryloxy" and "heteroaryloxyethoxy" shall be construed accordingly.

As used herein, the expression "heterocycle" or "saturated heterocyclic" includes all of the known reduced heteroatom containing cyclic radicals. Representative 5-membered heterocycle radicals include tetrahydrofuranyl, 1,3-dioxolanyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, pyranyl, 1,3-dioxanyl, thiomorpholinyl, and the like. Various other heterocycle radicals include, without limitation, aziridinyl, azepanyl, diazepanyl, diazabicyclo[2.2.1]hept-2-yl, and triazocanyl, and the like.

As used herein, the expression "$(C_6-C_{13})$bicyclic" includes all of the known bicyclic radicals. Representative examples of "bicyclic" includes without any limitation bicyclo[2.1.1]hexane, bicyclo[2.2.1]heptane, bicyclo[[3.2.1]octane, bicyclo[2.2.2]octane, bicyclo[3.2.2]nonane, bicyclo[3.3.1]nonane, bicyclo[3.3.2]decane, bicyclo[4.3.1]decane, bicyclo[4.4.1]undecane, bicyclo[5.4.1]dodecane, and the like. Derived expressions such as "bicycloalkoxy", "bicycloalkylalkyl", "bicycloalkylaryl", "bicycloalkylcarbonyl" are to be construed accordingly.

"Halogen" (or "halo") means chlorine (chloro), fluorine (fluoro), bromine (bromo), and iodine (iodo).

As used herein, "patient" means a warm blooded animal, such as for example rats, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di- acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

As used herein, the term "prodrug" shall have the generally accepted meaning in the art. One such definition includes a pharmacologically inactive chemical entity that when metabolized or chemically transformed by a biological system such as a mammalian system is converted into a pharmacologically active substance.

The expression "stereoisomers" is a general term used for all isomers of the individual molecules that differ only in the orientation of their atoms in space. Typically it includes mirror image isomers that are usually formed due to at least one asymmetric center (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

The term "solvate" as used herein means that an aggregate that consists of a solute ion or molecule with one or more solvent molecules. Similarly, a "hydrate" means that a solute ion or molecule with one or more water molecules.

In a broad sense, the term "substituted" is contemplated to include all permissible substituents of organic compounds. In a few of the specific embodiments as disclosed herein, the term "substituted" means substituted with one or more substituents independently selected from the group consisting of $(C_1-C_{20})$alkyl, $(C_2-C_6)$alkenyl, $(C_1-C_6)$perfluoroalkyl, phenyl, hydroxy, —$CO_2H$, an ester, an amide, $(C_1-C_6)$alkoxy, $(C_1-C_6)$thioalkyl, $(C_1-C_6)$perfluoroalkoxy, —$NH_2$, Cl, Br, I, F, CN, $SF_5$, —NH-lower alkyl, and —N(lower alkyl)$_2$, unless otherwise noted. However, any of the other suitable substituents known to one skilled in the art can also be used in these embodiments.

"Therapeutically effective amount" means an amount of the compound which is effective in treating the named disease, disorder or condition.

The term "treating" refers to:
(i) preventing a disease, disorder or condition from occurring in a patient that may be predisposed to the disease, disorder and/or condition, but has not yet been diagnosed as having it;
(ii) inhibiting the disease, disorder or condition, i.e., arresting its development; and (iii) relieving the disease, disorder or condition, i.e., causing regression of the disease, disorder and/or condition.

Thus, in accordance with the practice of this invention there is provided a compound of the formula I:

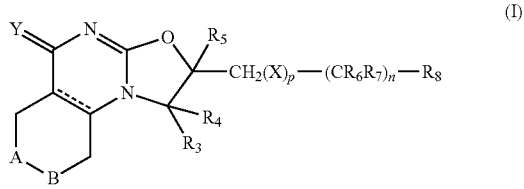

wherein:

---- is a single or a double bond;

p is 0 or 1;

n is an integer from 0 to 3;

X is oxygen, sulfur or $NR_{21}$, wherein $R_{21}$ is hydrogen or $(C_1-C_4)$alkyl;

Y is oxygen or sulfur;

A is a single covalent bond or $CHR_1$;

B is $CHR_2$, $NR_2$, oxygen or sulfur;

$R_1$ and $R_2$ are the same or different and independently of each other selected from the group consisting of hydrogen, $CF_3$, straight or branched chain $(C_1-C_{10})$alkyl, mono- or di-fluoro$(C_1-C_4)$alkyl, mono- or di-fluoro$(C_1-C_4)$alkoxy$(C_0-C_4)$alkyl, mono- or di-fluoro$(C_1-C_4)$alkylsulfanyl$(C_0-C_4)$alkyl, mono- or di-fluoro$(C_1-C_4)$alkylsulfinyl$(C_0-C_4)$alkyl, mono- or di-fluoro$(C_1-C_4)$alkylsulfonyl$(C_0-C_4)$alkyl, $(C_1-C_{10})$alkoxy$(C_0-C_4)$alkyl, $(C_1-C_{10})$alkylsulfanyl$(C_0-C_4)$alkyl, $(C_1-C_{10})$alkylsulfinyl$(C_0-C_4)$alkyl, $(C_1-C_{10})$alkylsulfonyl$(C_0-C_4)$alkyl, $(C_1-C_{10})$alkoxy mono- or di-fluoro$(C_1-C_4)$alkyl, $(C_1-C_{10})$alkylsulfanyl mono- or di-fluoro$(C_1-C_4)$alkyl, $(C_1-C_{10})$alkylsulfinyl mono- or di-fluoro$(C_1-C_4)$alkyl, $(C_1-C_{10})$alkylsulfonyl mono- or di-fluoro$(C_1-C_4)$alkyl, $(C_6,C_{10})$aryl$(C_0-C_4)$alkyl, $(C_6,C_{10})$aryl mono- or difluoro$(C_1-C_4)$alkyl, $(C_6,C_{10})$aryl mono- or difluoro$(C_2-C_4)$alkyloxy, $(C_6,C_{10})$aryloxy$(C_0-C_4)$alkyl, $(C_6,C_{10})$arylsulfanyl$(C_0-C_4)$alkyl, $(C_6,C_{10})$arylsulfinyl$(C_0-C_4)$alkyl, $(C_6,C_{1-})$arylsulfonyl$(C_0-C_4)$alkyl, $(C_3-C_8)$cycloalkyl$(C_0-C_4)$alkyl, mono- or difluoro$(C_3-C_8)$cycloalkyl$(C_0-C_4)$alkyl, $(C_3-C_8)$cycloalkoxy$(C_0-C_4)$alkyl, mono- or difluoro$(C_3-C_8)$cycloalkyloxy$(C_0-C_4)$alkyl, $(C_3-C_8)$cycloalkyl mono- or difluoro$(C_1-C_4)$alkyl, $(C_3-C_8)$cycloalkyl mono- or difluoro$(C_2-C_4)$alkyloxy, $(C_3-C_8)$cycloalkylsulfanyl$(C_0-C_4)$alkyl, $(C_3-C_8)$cycloalkylsulfinyl$(C_0-C_4)$alkyl, $(C_3-C_8)$cycloalkylsulfonyl$(C_0-C_4)$alkyl, hydroxy$(C_1-C_4)$alkyl, heteroaryl$(C_0-C_4)$alkyl, heteroaryl mono- or difluoro$(C_1-C_4)$alkyl, heteroaryloxy$(C_0-C_4)$alkyl, heteroaryloxy mono- or difluoro$(C_2-C_4)$alkyl, heteroarylsulfanyl$(C_0-C_4)$alkyl, heteroarylsulfinyl$(C_0-C_4)$alkyl, heteroarylsulfonyl$(C_0-C_4)$alkyl, saturated heterocyclic$(C_0-C_4)$alkyl, saturated heterocyclic mono- or di-fluoro$(C_1-C_4)$alkyl, saturated heterocyclyloxy$(C_0-C_4)$alkyl, saturated heterocyclyloxy mono- or di-fluoro$(C_2-C_4)$alkyl, saturated heterocyclylsulfanyl$(C_0-C_4)$alkyl, heterocyclylsulfinyl$(C_0-C_4)$alkyl, heterocyclylsulfonyl$(C_0-C_4)$alkyl, $—CO_2R_{22}$ or $—CONR_{23}R_{24}$ wherein $R_{22}$, $R_{23}$ and $R_{24}$ are the same or different and independently of each other selected from hydrogen or $(C_1-C_4)$alkyl; and wherein $R_1$ and $R_2$ are optionally further substituted;

$R_3$ and $R_4$ are the same or different and independently of each other selected from the group consisting of hydrogen, $(C_1-C_4)$alkyl, $(C_3-C_8)$cycloalkyl and $(C_6,C_{10})$aryl $(C_1-C_4)$alkyl; or $R_3$ and $R_4$ taken together with the carbon atom to which they are attached form a substituted or unsubstituted $C_5-C_7$ carbocyclic ring;

$R_5$, $R_6$ and $R_7$ are the same or different and independently of each other selected from the group consisting of hydrogen, $(C_1-C_4)$alkyl and $(C_3-C_8)$cycloalkyl;

$R_8$ is selected from the group consisting of substituted or unsubstituted phenyl, substituted or unsubstituted naphthyl, substituted or unsubstituted indanyl, substituted or unsubstituted tetralinyl, substituted or unsubstituted benzocycloheptanyl, substituted or unsubstituted hexahydrofluorenyl, substituted or unsubstituted $(C_3-C_8)$cycloalkyl, substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, substituted or unsubstituted tetrahydrodibenzofuranyl and substituted or unsubstituted hexahydrodibenzofuranyl;

wherein said substituents are selected from the group consisting of $CF_3$, $OCF_3$, halogen, $CN$, $SF_5$, straight or branched chain $(C_1-C_{20})$alkyl, $(C_1-C_4)$alkylsulfonyl, substituted or unsubstituted $(C_3-C_{10})$cycloalkyl $(CR_9R_{10})_m$, substituted or unsubstituted $(C_6-C_{16})$spirocycloalkyl, substituted or unsubstituted $(C_6,C_{10})$aryl $(CR_9R_{10})_m$, substituted or unsubstituted heteroaryl $(CR_9R_{10})_m$, substituted or unsubstituted $(C_6,C_{10})$aryl $(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_3-C_{10})$cycloalkoxy, substituted or unsubstituted $(C_6,C_{10})$aryloxy, substituted or unsubstituted heteroaryloxy, substituted or unsubstituted piperidinyl$(CR_9R_{10})_m$, substituted or unsubstituted piperazinyl$(CR_9R_{10})_m$, substituted or unsubstituted $(C_4-C_7)$lactam, substituted or unsubstituted tetrahydropyranyl$(CR_9R_{10})_m$, substituted or unsubstituted tetrahydrofuranyl$(CR_9R_{10})_m$, substituted or unsubstituted 1,3-dioxanyl, substituted or unsubstituted 1,3-dioxolanyl, $(C_1-C_4)$alkoxyethoxy, substituted or unsubstituted $(C_3-C_8)$cycloalkyloxyethoxy, substituted or unsubstituted $(C_6,C_{10})$aryloxyethoxy and substituted or unsubstituted heteroaryloxyethoxy;

wherein m is an integer from 0 to 10;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ carbocyclic ring;

and wherein said substituents are selected from the aforementioned substituents.

The compound of formula I can be present as a salt. It can also present as an enantiomer, a stereoisomer or a tautomer or a racemic mixture thereof. All of these forms are part of this invention.

However, with the proviso that:
when ----- is a double bond, X and Y are oxygen, p is 1, n is 0, A is a single covalent bond or A is $CHR_1$, B is $CHR_2$, and wherein $R_1$, $R_2$, $R_3$, $R_4$ and $R_5$ are hydrogen, then $R_8$ is not phenyl or 4-ethylphenyl; and when ----- is a double bond, X and Y are oxygen, p and n are 0, A is a single covalent bond or A is $CHR_1$, B is $CHR_2$, and wherein $R_1$, $R_2$, $R_3$, $R_4$ and $R_5$ are hydrogen, then $R_8$ is not piperidine.

More specifically, the following compounds are excluded from this invention:
5,6,7,8-tetrahydro-2-phenoxymethyl-9H-cyclohexa[1,2-e]oxazolo[3,2-a]pyrimidin-9-one;
5,6,7,8-tetrahydro-2-(4-ethylphenoxymethyl)-9H-cyclohexa[1,2-e]oxazolo[3,2-a]pyrimidin-9-one;
5,6,7,8-tetrahydro-2-(1-piperidinomethyl)-9H-cyclohexa[1,2-e]oxazolo[3,2-a]pyrimidin-9-one;
5,6,7-trihydro-2-phenoxymethyl-8H-cyclopenta[1,2-e]oxazolo[3,2-a]pyrimidin-8-one;
5,6,7-trihydro-2-(4-ethylphenoxymethyl)-8H-cyclopenta[1,2-e]oxazolo[3,2-a]pyrimidin-8-one; and
5,6,7-trihydro-2-(piperidinomethyl-8H-cyclopenta[1,2-e]oxazolo[3,2-a]pyrimidin-8-one.

The compounds that are excluded from this invention are known in the prior art. See, Adetchessi et al., Tetrahedron 61 (2005) 4453-4460. It should further be noted that a few of the substituted dihydro and tetrahydro oxazolopyrimidinones, which are structurally analogous to compounds of this invention are also known. For instance, see Forfar et. al., J. Heterocyclic Chem., 38, 823-827 (2001), and Forfar et. al., Arch. Pharm. (Weinheim), 323, 905-909 (1990). All of these references are incorporated herein by reference in their entirety.

As also noted above, various substituents as defined for formula (I) can further be optionally substituted by any of the art recognized substituents some of which are generically described herein and a few of the specific substituents are enumerated by way of specific examples. More particularly, various $R_1$ and $R_2$ as described herein can further be optionally substituted with one or more substituents as described herein.

In an embodiment of this invention the compound of formula (I) of this invention has the following substituents:
----- is a double bond;
p is 1;
n is 0;
X and Y are oxygen;
A is a single covalent bond or $CHR_1$;
B is $CHR_2$ or $NR_2$;
$R_1$ and $R_2$ are the same or different and independently of each other selected from hydrogen, $CF_3$, straight or branched $(C_1-C_{10})$alkyl, mono- or di-fluoro$(C_1-C_4)$alkyl, mono- or di-fluoro$(C_1-C_4)$alkoxy$(C_0-C_4)$alkyl, $(C_1-C_{10})$alkoxy$(C_0-C_4)$alkyl, $(C_6,C_{10})$aryl, $(C_6,C_{10})$aryl$(C_1-C_4)$alkyl $(C_3-C_8)$cycloalkyl$(C_0-C_4)$alkyl, $(C_3-C_8)$cycloalkoxy$(C_0-C_4)$alkyl, hydroxy$(C_1-C_4)$alkyl or —$CO_2C_2H_5$;
$R_3$, $R_4$ and $R_5$ are hydrogen;
$R_8$ is selected from the group consisting of substituted or unsubstituted phenyl, substituted or unsubstituted indanyl, substituted or unsubstituted tetralinyl, substituted or unsubstituted benzocycloheptanyl, substituted or unsubstituted hexahydrofluorenyl and substituted or unsubstituted cyclohexyl; wherein said substituents are selected from the group consisting of $CF_3$, $OCF_3$, $SF_5$, fluorine, chlorine, bromine, CN, straight or branched chain $(C_1-C_{20})$alkyl, substituted or unsubstituted $(C_3-C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$ alkoxy, substituted or unsubstituted $(C_3-C_{10})$cycloalkoxy, substituted or unsubstituted $(C_6,C_{10})$aryloxy, substituted or unsubstituted heteroaryloxy, and substituted or unsubstituted tetrahydropyranyl$(CR_9R_{10})_m$;
wherein
m is an integer from 0 to 2;
$R_9$ and $R_{10}$ are the same or different and independently of each other chosen from hydrogen or $(C_1-C_4)$alkyl; or
$R_9$ and $R_{10}$ taken together with the carbon atom to which they are attached form a substituted or unsubstituted $C_3-C_8$ ring.

As noted above, the substituents of $R_8$ moiety can be any of the suitable art recognized substituents including the specific moieties enumerated for $R_8$ above. Further, this embodiment of the invention includes compound of formula (I) in the salt form as well as it can also present in any of the stereoisomeric form including an enantiomer, stereoisomer or a tautomer thereof or a racemic mixture thereof.

In another embodiment, the compound of this invention can be represented by formula II:

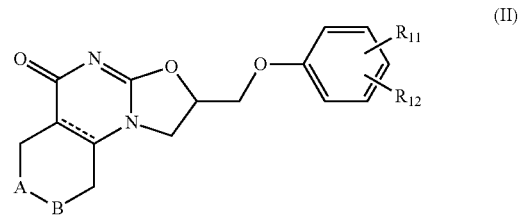

(II)

wherein:
----- is a single or a double bond;
A is a single covalent bond;
B is $CHR_2$ or $NR_2$;
$R_1$ and $R_2$ are the same or different and independently of each other selected from hydrogen, $CF_3$, straight or branched $(C_1-C_{10})$alkyl, mono- or di-fluoro$(C_1-C_4)$alkyl, mono- or di-fluoro$(C_1-C_4)$alkoxy$(C_0-C_4)$alkyl, $(C_1-C_{10})$alkoxy$(C_0-C_4)$alkyl, $(C_6,C_{10})$aryl, $(C_6,C_{10})$aryl$(C_1-C_4)$alkyl, phenylsulfanyl$(C_0-C_4)$alkyl, phenylsulfinyl$(C_0-C_4)$alkyl, phenylsulfonyl$(C_0-C_4)$alkyl, $(C_3-C_8)$cycloalkyl$(C_0-C_4)$alkyl, $(C_3-C_8)$cycloalkoxy$(C_0-C_4)$alkyl, hydroxy$(C_1-C_4)$alkyl or —$CO_2C_2H_5$;
$R_{11}$ and $R_{12}$ are the same or different and independently of each other selected from the group consisting of $CF_3$, $OCF_3$, $SF_5$, fluorine, chlorine, bromine, CN, straight or branched chain $(C_1-C_{20})$alkyl, substituted or unsubstituted $(C_3-C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain ($C_1$-$C_{20}$)alkoxy, substituted or unsubstituted ($C_3$-$C_{10}$)cycloalkoxy, substituted or unsubstituted tetrahydropyranyl($CR_9R_{10}$)$_m$, substituted or unsubstituted ($C_6$,$C_{10}$)aryloxy and substituted or unsubstituted heteroaryloxy; and wherein m is 0 or 1;

$R_9$ and $R_{10}$ are the same or different and independently of each other chosen from hydrogen or ($C_1$-$C_4$)alkyl;

Again, the substituents on some of the groups listed for $R_{11}$ and $R_{12}$ can be same as the ones listed for $R_{11}$ and $R_{12}$ or any of the suitable art recognized substituents can be used as described herein. For instance, said substituents are selected from the group consisting of halogen, straight or branched chain ($C_1$-$C_{10}$)alkyl, phenyl, indanyl and imidazolyl. The compound of formula (II) can be present in the form of a salt. Also, this invention encompasses an enantiomer, stereoisomer or a tautomer or a racemic mixture of compound of formula (II).

As specific examples of compound of formula (II) of this embodiment, the following compound may be enumerated without any limitations:

2-(4-cyclohexyl-phenoxymethyl)-1,2,7,8-tetrahydro-6H-3-oxa-4,8b-diaza-as-indacen-5-one.

The above enumerated compound can also present in the form of a salt as well as an enantiomer, stereoisomer or a tautomer thereof or a racemic mixture thereof; all of which are part of this invention.

In another embodiment, the compound of this invention can be represented by formula II:

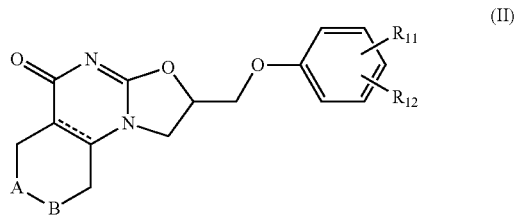

(II)

wherein:

----- is a single or a double bond;

A is $CHR_1$;

B is $CHR_2$ or $NR_2$;

$R_1$ and $R_2$ are the same or different and independently of each other selected from hydrogen, $CF_3$, straight or branched ($C_1$-$C_{10}$)alkyl, mono- or di-fluoro($C_1$-$C_4$)alkyl, mono- or di-fluoro($C_1$-$C_4$)alkoxy($C_0$-$C_4$)alkyl, ($C_1$-$C_{10}$)alkoxy($C_0$-$C_4$)alkyl, ($C_6$,$C_{10}$)aryl, ($C_6$,$C_{10}$)aryl($C_1$-$C_4$)alkyl, phenylsulfanyl($C_0$-$C_4$)alkyl, phenylsulfinyl($C_0$-$C_4$)alkyl, phenylsulfonyl($C_0$-$C_4$)alkyl, ($C_3$-$C_8$)cycloalkyl($C_0$-$C_4$)alkyl, ($C_3$-$C_8$)cycloalkoxy($C_0$-$C_4$)alkyl, hydroxy($C_1$-$C_4$)alkyl or —$CO_2C_2H_5$;

$R_{11}$ and $R_{12}$ are the same or different and independently of each other selected from the group consisting of $CF_3$, $OCF_3$, $SF_5$, fluorine, chlorine, bromine, CN, straight or branched chain ($C_1$-$C_{20}$)alkyl, substituted or unsubstituted ($C_3$-$C_{10}$)cycloalkyl($CR_9R_{10}$)$_m$, substituted or unsubstituted ($C_6$,$C_{10}$)aryl($CR_9R_{10}$)$_m$, substituted or unsubstituted ($C_6$,$C_{10}$)aryl($C_3$-$C_8$)cycloalkyl, substituted or unsubstituted ($C_8$-$C_{13}$)bicyclic, substituted or unsubstituted adamantyl, substituted or unsubstituted indanyl, substituted or unsubstituted tetralinyl, substituted or unsubstituted benzocycloheptyl, straight or branched chain ($C_1$-$C_{20}$)alkoxy, substituted or unsubstituted ($C_3$-$C_{10}$)cycloalkoxy, substituted or unsubstituted tetrahydropyranyl($CR_9R_{10}$)$_m$, substituted or unsubstituted ($C_6$,$C_{10}$)aryloxy and substituted or unsubstituted heteroaryloxy; and wherein m is 0 or 1;

$R_9$ and $R_{10}$ are the same or different and independently of each other chosen from hydrogen or ($C_1$-$C_4$)alkyl;

Again, the substituents on some of the groups listed for $R_{11}$ and $R_{12}$ can be same as the ones listed for $R_{11}$ and $R_{12}$ or any of the suitable art recognized substituents can be used as described herein. For instance, said substituents are selected from the group consisting of halogen, straight or branched chain ($C_1$-$C_{10}$)alkyl, phenyl, indanyl and imidazolyl. The compound of formula (II) can be present in the form of a salt. Also, this invention encompasses an enantiomer, stereoisomer or a tautomer or a racemic mixture of compound of formula (II).

As specific examples of compound of formula (II) of this embodiment, the following compound may be enumerated without any limitations:

2-(4-cyclohexyl-phenoxymethyl)-1,2,6,7,8,9-hexahydro-oxazolo[3,2-a]quinazolin-5-one.

The above compound can present in the form of a salt or as an enantiomer, stereoisomer or a tautomer or as a racemic mixture.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein.

More specifically, the compounds disclosed herein can be synthesized according to the procedures of Adetchessi et al., Tetrahedron 61 (2005) 4453-4460 by employing the appropriate starting materials. Several of the intermediates used in the preparation of the compound of formula (I) are known and can be prepared in accordance with the procedures known to one skilled in the art. A few other intermediates can also be prepared in accordance with the procedures described herein (Schemes A-C) or by any of the procedures known in the art.

Schemes A through C illustrate preparation of a few of the starting alcohols in which n is 0 and $R_8$ is a substituted phenyl. Thus, Schemes A through C describe syntheses of a variety of phenols that can be used as starting alcohols of formula (VIII).

For instance, Scheme A illustrates preparation of phenols of formula (VIIIa) employing 4-benzyloxy-bromo-benzene as the starting material. In Step A1, Scheme A, 4-benzyloxy-bromo-benzene is first converted to a Grignard reagent by reacting with magnesium which is then reacted with a cyclic ketone of formula (XIV), where Z=$CH_2$ or oxygen and m=0, 1 or 2, to form a compound of formula (XV). The Grignard reaction is generally carried out in an ethereal solvent, such as tetrahydrofuran (THF) or diethyl ether. The Grignard reagent thus formed is then reacted with a cyclic ketone of formula (XIV), which results in an alcohol of formula (XV).

Scheme A

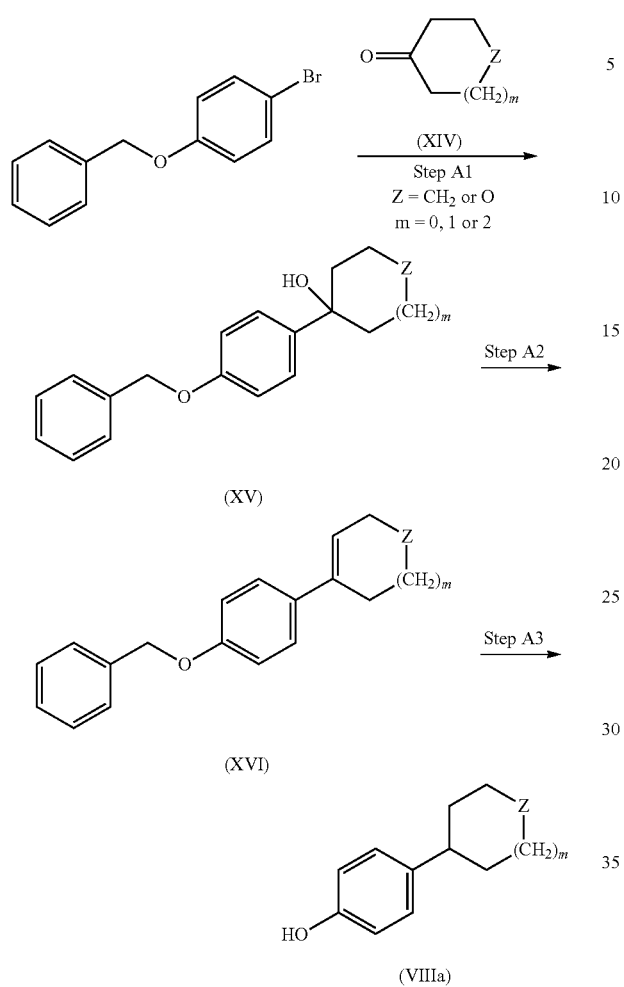

(VIIIa)

In Step A2, Scheme A, the compound of formula (XV) is subjected to a dehydration reaction under suitable reaction conditions to form a compound of formula (XVI). Such dehydration reactions are generally carried out in an alcoholic solvent such as ethanol in the presence of an acid catalyst such as hydrochloric acid. This reaction can be carried out at a reaction temperature in the range of from about sub-ambient to super-ambient temperatures. For instance, a temperature range of from about 30° C. to about 60° C. can be employed. Finally, in Step A3, Scheme A, the compound of formula (XVI) is subjected to reductive cleavage reaction to form the substituted phenolic compound of formula (VIIIa). The reductive cleavage reactions can be carried out using any of the known procedures in the art. For instance, such reductive cleavage can be effected by employing hydrogenation catalyst such as palladium on activated carbon in a hydrogen atmosphere.

Scheme B illustrates another preparative method for the preparation of a substituted phenolic compound of formula (VIIIb), which can also be used as a starting alcohol in the synthesis of compounds of formula (I). The phenolic compound of formula (VIIIb) is primarily substituted with a nitrogen heterocycle, which can readily be synthesized by an electrophilic substitution of anisole under acidic conditions as shown in Scheme B.

Scheme B

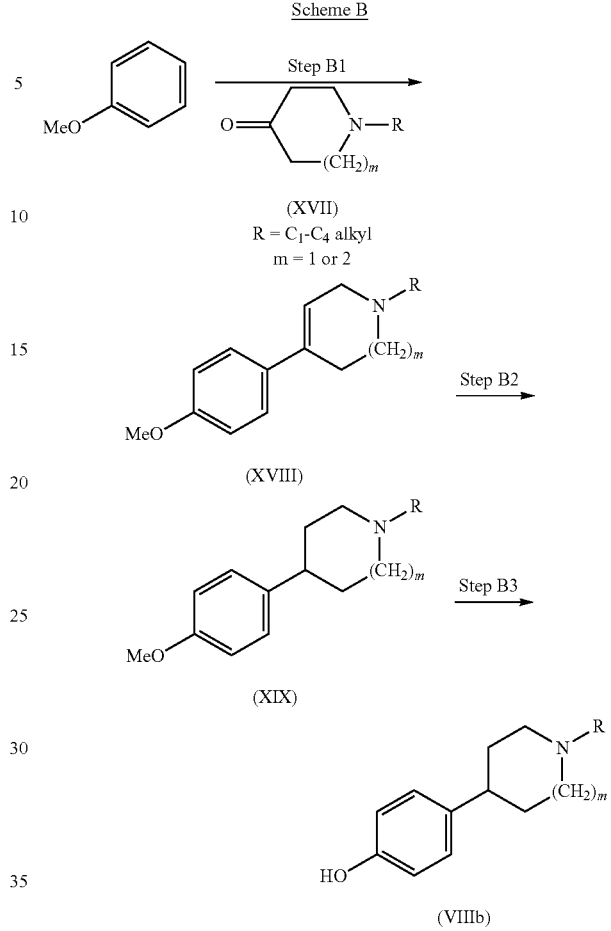

(VIIIb)

In Step B1, Scheme B, anisole is subjected to an electrophilic substitution reaction with an oxo-nitrogen heterocycle of formula (XVII), where R is $C_1$-$C_4$ alkyl and m=1 or 2. Any of the known electrophilic substitution reaction conditions can be employed in this step. For example, anisole is reacted with compound of formula (XVII) in the presence of hydrochloric acid to obtain compound of formula (XVIII), which in turn is subjected to hydrogenation reaction to form compound of formula (XIX). For instance, such a hydrogenation reaction can be carried out catalytically using palladium on activated carbon in a hydrogen atmosphere. Finally, the compound of formula (XIX) is subjected to demethylation reaction to form free phenolic compound of formula (VIIIb). Various known dealkylation, preferably, demethylation reaction conditions can be employed for this purpose. One such example include reacting compound of formula (XIX) with an acid such as hydrobromic acid to form compound of formula (VIIIb).

Finally, Scheme C illustrates a preparation of a phenolic compound of formula (VIIIe). In this illustration, in Step C1, Scheme C, a series of phenolic compounds of formula (VIIIc) can be prepared by employing an alcohol of formula (XX), which is reacted with phenol in the presence of a suitable acid catalyst, such as p-toluenesulfonic acid to form phenolic compound of formula (VIIIc). As illustrated herein, the substituents $R_d$, $R_e$ and $R_f$ are any of the feasible substituents as described herein.

Scheme C

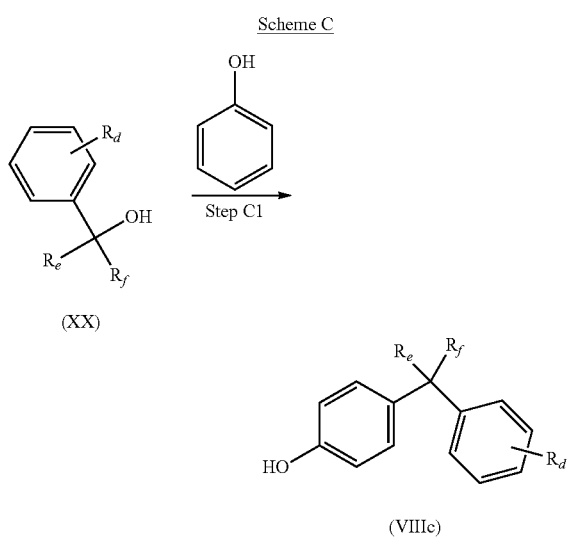

(XX)

(VIIIc)

In another aspect of this embodiment, this invention also relates to a method of modulating one or more metabotropic glutamate receptor functions in a patient requiring such treatment. Such a method involves administering an effective amount of a compound of formula (I) or a pharmaceutically acceptable salt, an enantiomer, a stereoisomer or a tautomer thereof or a racemic mixture thereof.

In a further embodiment, this invention also involves a method of treating a specific disease, a disorder or a condition using an effective amount of a compound of formula (I) of this invention. Specific diseases that can be treated using the compounds of formula (I) of this invention include, without any limitation, neurological or psychiatric disorders.

As used herein "psychiatric disorders" shall have the same meaning as "psychotic disorder" as defined in Diagnostic and Statistical Manual of Mental Disorders, 4th Ed., ("DSM-IV") American Psychiatric Association, 1995, incorporated herein by reference. The essential feature of brief psychotic disorder is a disturbance that involves the sudden onset of at least one of the following positive psychotic symptoms: delusions, hallucinations, disorganized speech, (e.g., frequent derailment or incoherence), or grossly disorganized or catatonic behavior (Criterion A). An episode of the disturbance lasts at least one day but less than one month, and the individual eventually has a full return to the premorbid level of functioning (Criterion B). The disturbance is not better accounted for by a mood disorder with psychotic features, by schizoaffective disorder, or by schizophrenia and is not due to the direct physiological effects of a substance (e.g., hallucinogen) or a general medical condition (e.g., subdural hematoma) (Criterion C). It should further be noted that a skilled artisan recognizes that there are alternative nomenclatures, nosologies, and classification systems for neurological and psychiatric disorders described herein and that these systems evolve with medical scientific progress.

It is also recognized that one skilled in the art may affect the neurological and psychiatric disorders by treating a patient presently afflicted with the disorders or by prophylactically treating a patient afflicted with the disorders with an effective amount of the compound of formula (I) of this invention. Thus, the terms "treatment" and "treating" are intended to refer to all processes wherein there may be a slowing, interrupting, arresting, controlling, or stopping of the progression of the neurological and psychiatric disorders described herein, but does not necessarily indicate a total elimination of all disorder symptoms, and is intended to include prophylactic treatment of such neurological and psychiatric disorders.

In a further embodiment of this invention, specific diseases that can be treated using the compounds of formula (I) of this invention include without any limitation: anxiety, migraine, schizophrenia, epilepsy and pain.

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease involving the effects of metabotropic glutamate receptor functions. That is, the compounds of the present invention are modulators of metabotropic glutamate receptors (mGluR), particularly, mGluR2, and may be effectively administered to ameliorate any disease state which is mediated all or in part by mGluR2.

All of the various embodiments of the compounds used in the methods of this invention as disclosed herein can be used in the method of treating various disease states as described herein. As stated herein, the compounds used in the method of this invention are capable of modulating the effects of mGluR2 and thereby alleviating the effects and/or conditions caused due to the activity of mGluR2. In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal, intracerebroventricular (icv) or topical route.

Finally, in yet another embodiment of this invention, there is also provided a pharmaceutical composition comprising a pharmaceutically acceptable carrier and a compound of formula (I) of this invention, including enantiomers, stereoisomers, and tautomers of said compound and pharmaceutically acceptable salts, solvates or derivatives thereof, with said compound having the general structure shown in formula I as described herein.

As described herein, the pharmaceutical compositions of this invention feature modulation of mGluR2 and thus are useful in treating any disease, condition or a disorder involving the effects of mGluR2 in a patient. Again, as described above, all of the preferred embodiments of the compounds of this invention as disclosed herein can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of formula (I) of the present invention, or a pharmaceutically acceptable salt thereof.

When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal, intracerebroventricular (icy) or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES

General

Reactions generally are run under a nitrogen atmosphere. Solvents are dried over sodium or magnesium sulfate and are evaporated under vacuum on a rotary evaporator. TLC analyses are performed with EM Science silica gel 60 F254 plates with visualization by UV irradiation wherever possible. Flash chromatography is performed using Isco prepacked silica gel cartridges. The $^1$H NMR spectra are run at 300 MHz on a Gemini 300 or Varian VXR 300 spectrometer and are determined in a deuterated solvent, such as DMSO-$d_6$ or CDCl$_3$ unless otherwise noted. Chemical shifts values are indicated in parts per million (ppm) with reference to tetramethylsilane (TMS) as the internal standard. The LC/MS are run on a Micromass Platform LCZ.

As used in the examples and preparations that follow, the terms used therein shall have the meanings indicated: "kg" refers to kilograms, "g" refers to grams, "mg" refers to milligrams, "µg" refers to micrograms, "pg" refers to picograms, "lb" refers to pounds, "oz" refers to ounces, "mol" refers to moles, "mmol" refers to millimoles, "µmole" refers to micromoles, "nmole" refers to nanomoles, "L" refers to liters, "mL" or "ml" refers to milliliters, "µL" refers to microliters, "gal" refers to gallons, "° C." refers to degrees Celsius, "R$_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "THF" refers to tetrahydrofuran, "DMF" refers to dimethylformamide, "NMP" refers to 1-methyl-2-pyrrolidinone, "EtOH" refers to ethyl alcohol, "MeOH" refers to methyl alcohol, "EtOAc" refers to ethyl acetate; "brine" refers to a saturated aqueous sodium chloride solution, "M" refers to molar, "mM" refers to millimolar, "µM" refers to micromolar, "nM" refers to nanomolar, "N" refers to normal, "TLC" refers to thin layer chromatography, "HPLC" refers to high performance liquid chromatography, "i.p." refers to intraperitoneally, "i.v." refers to intravenously, anhyd=anhydrous; aq=aqueous; min=minute; mins=minutes; h or hr=hour; d=day; psi=pounds per square inch; atm=atmosphere; sat.=saturated; s=singlet, d=doublet; t=triplet; q=quartet; m=multiplet; dd=doublet of doublets; br=broad; LC=liquid chromatograph; MS=mass spectrograph; ESI=electrospray ionization; CI=chemical ionization; RT=retention time; M=molecular ion.

Example 1

2-(4-Cyclohexyl-phenoxymethyl)-1,2,7,8-tetrahydro-6H-3-oxa-4,8b-diaza-as-indacen-5-one

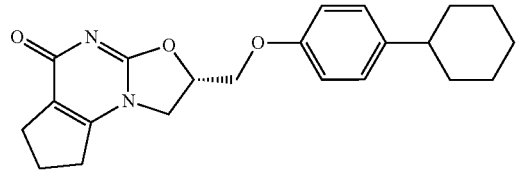

Step 1: 2-(4-Cyclohexyl-phenoxymethyl)-oxirane

To a mixture of R-epichlorohydrin (9.8 g, 106 mmol) and 4-cyclohexylphenol (3.73 g, 21.2 mmol) in acetonitrile (40 ml) was added cesium carbonate (6.9 g, 21.2 mmol). The mixture was heated at reflux for 3 hours. The reaction mixture was cooled, poured into water (100 mL) and extracted twice with EtOAc. The organic phases were combined and washed with water, brine, dried (Na$_2$SO$_4$), concentrated and dried under high vacuum overnight to give the title compound.

Step 2: (5)-5-(4-Cyclohexyl-phenoxymethyl)-4,5-dihydro-oxazol-2-ylamine

To a vigorously stirred solution of sodium hydrogen cyanamide (0.64 g, 10 mmol) in methanol (10 mL) was added dropwise 2-(4-cyclohexyl-phenoxymethyl)-oxirane (2.32 g, 10 mmol) after which the reaction mixture was stirred at room temperature overnight. The reaction mixture was concentrated to remove methanol. Anhydrous diethyl ether (50 mL) was added after which the resulting white precipitate was removed by filtration through celite and the filtrate concentrated. The residue was purified by flash chromatography (silica, 7N $NH_3$ in methanol/methylene chloride) to give the title compound.

Step 3: 2-(4-Cyclohexyl-phenoxymethyl)-1,2,7,8-tetrahydro-6H-3-oxa-4,8b-diaza-as-indacen-5-one The title compound was prepared from (S)-5-(4-cyclohexyl-phenoxymethyl)-4,5-dihydro-oxazol-2-ylamine and 2-oxo-cyclopentanecarboxylic acid ethyl ester in accordance with the procedures of O.-S. Adetchessi, et. al., *Tetrahedron*, 61, (2005), 4453-4460. $C_{22}H_{26}N_2O_3$ (366.19), LCMS (ESI): 367.16 ($M^+$+H).
$^1$H NMR (CDCl$_3$, 300 MHz), δ 7.14 (d, 2H), 6.81 (d, 2H), 5.24 (m, 1H), 4.21-4.37 (m, 4H), 2.75-2.89 (m, 4H), 2.45 (m, 1H), 2.17 (m, 2H), 1.67-1.91 (m, 5H), 1.23-1.49 (m, 5H).

Example 2

2-(4-Cyclohexyl-phenoxymethyl)-1,2,6,7,8,9-hexahydro-oxazolo[3,2-a]quinazolin-5-one

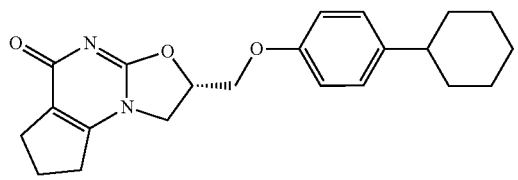

The title compound was prepared from (S)-5-(4-cyclohexyl-phenoxymethyl)-4,5-dihydro-oxazol-2-ylamine and 2-oxo-cyclopentanecarboxylic acid ethyl ester in accordance with the procedures of O.-S. Adetchessi, et. al., *Tetrahedron*, 61, (2005), 4453-4460. $C_{23}H_{28}N_2O_3$ (380.20), LCMS (ESI): 381.18 ($M^+$+H).
$^1$H NMR (CDCl$_3$, 300 MHz), δ 7.14 (d, 2H), 6.81 (d, 2H), 5.21 (m, 1H), 4.16-4.33 (m, 4H), 2.46 (m, 5H), 1.66-1.91 (m, 9H), 1.18-1.47 (m, 5H).

Biological Examples

Example 3

A calcium ion ($Ca^{2+}$) mobilization assay was used to identify and determine the activity for allosteric modulators of the rat or human mGluR2 receptor. Two formats were used: (1) examine the ability of glutamate to affect the potency of the modulator, by looking at a concentration-response curve of compound at different submaximal glutamate concentrations, and (2) look at the ability of the modulator to affect the potency of glutamate by looking at a concentration-response curve of glutamate at a maximal modulator concentration.

To monitor functional receptor response using calcium mobilization, a cell line stably expressing the rat or human mGluR2 receptor (normally coupled to its intracellular effector molecules through an inhibitory G-protein, Gαi) and Gα$_{16}$, in a tetracycline-inducible vector was created. Gα16 can promiscuously couple Gs and Gi-coupled receptors to the inositol phospholipid signaling pathway by activating phospholipase Cβ resulting in a $Ca^{2+}$ signal (normally Gαq-mediated), that can be monitored with fluorescence plate readers such as FLIPR (Molecular Devices, Fluorescence Imaging Plate Reader), FDSS6000 (Hamamatsu, Fluorescence Drug Screening System), or FlexStation (Molecular Devices). The $Ca^{2+}$ mobilization assay was based on the detection of intracellular calcium changes using a selective, calcium-chelating dye: Fluo-3, Fluo-4, or Calcium-3. A large fluorescence intensity increase was observed upon calcium association with the dye. The dye was delivered either with the acetoxymethyl ester, and washed off, or using a no-wash kit (Molecular Devices). Fluorescence signals stimulated by glutamate were recorded and used to generate the following pharmacological parameters: (1) the potency (EC50) of the compound(s) of interest at approx. EC10 for glutamate at the rat and human mGluR2 receptors respectively, and (2) a fold-shift of the glutamate EC50 by maximal concentration of compound(s) of interest.

The compounds of formula (I) of this invention tested in accordance with this procedure exhibited the potency (EC50) in the range of from about 3 micromolar (μM) to about 0.5 nanomolar (nM).

The efficacy of the compounds of formula (I) of this invention in treating a variety of diseases as disclosed herein can be confirmed by any of the methods known to one skilled in the art. For instance, the efficacy in treating anxiety can be confirmed by using Vogel conflict test. See, for example, Tatarczynska et al., Psychopharmacology (Berl). 2001 October; 158(1):94-9 incorporated herein by reference in its entirety. Specifically, Tatarczynska et al. discloses the antianxiety-like effects of antagonists of group I and agonists of group II and III metabotropic glutamate receptors.

The preclinical anxiety and psychosis models also include stress induced hyperthermia, fear potentiated startle and PCP-induced hyperlocomotion. See Rorick-Kehn et al., J. Pharmacol. Exp. Ther. 2006 February; 316(2):905-13. Epub Oct. 13, 2005. Also see, Johnson et al., Psychopharmacology (Berl). 2005 April; 179(1):271-83. Epub Feb. 17, 2005. Fear-potentiated startle and elevated plus maze models have been used by Helton et al., J Pharmacol Exp Ther. 1998 February; 284(2):651-660 in order to demonstrate the anxiolytic and side-effect profile of LY354740: a potent, highly selective, orally active agonist for group II metabotropic glutamate receptors.

Various anxiety models to show efficacy in humans are also known in the art. See Kellner et al., Psychopharmacology (Berl). 2005 April; 179(1):310-5. Epub Sep. 30, 2004, where the effects of a metabotropic glutamate(2/3) receptor agonist on panic anxiety induced by cholecystokinin tetrapeptide in healthy humans has been reported.

In addition, the efficacy of the compounds of formula (I) of this invention in treating schizophrenia may also be ascertained by various known models in the art. For instance, PCP-induced hyperlocomotion, PCP-disrupted prepulse inhibition, stress-induced hyperthermia, and elevated plus maze models have been used to demonstrate the efficacy of allosteric modulators of mGluR2. See, Galici et al., J Pharmacol Exp Ther. 2006 July; 318(1):173-85. Epub Apr. 11, 2006, where it is shown that biphenyl-indanone A, a positive allosteric modulator of the mGluR2, has antipsychotic- and anxiolytic-like effects in mice.

The efficacy of the compounds of formula (I) of this invention in improving the working memory in humans can be ascertained by a variety of methods known in the art. For instance, Krystal et al., Psychopharmacology (Berl). 2005 April; 179(1):303-9. Epub Aug. 10, 2004, reported that the attenuation of the disruptive effects of the NMDA glutamate receptor antagonist, ketamine, on working memory by pretreatment with the group II metabotropic glutamate receptor agonist, LY354740, in healthy human subjects. In another example, Patil et al., Nature Medicine. 2007 September; 13(9):1102-7. Epub Sep. 2, 2007. reported that the group II metabotropic glutamate receptor agonist, LY2140023, showed statistically significant improvements in both positive and negative symptoms of schizophrenia compared to placebo.

The compounds of formula (I) of this invention are also useful in treating sleep disorders and depression. Feinberg et al., Pharmacol Biochem Behav. 2002, 73(2) 467-74, have reported that the selective group mGluR2/3 receptor agonist, LY379268, suppresses rapid eye movement (REM) sleep and fast EEG in the rat. Gewirtz et al., Pharmacol Biochem Behav. 2002 September; 73(2):317-26, have examined the effects of mGluR2/3 agonists on BDNF mRNA expression in medial prefrontal cortex induced by the hallucinogen and $5HT_{2A/2B/2C}$ agonist. Also, see Schechter et al., NeuroRx. 2005 October; 2(4):590-611. Review, where innovative approaches for the development of antidepressant drugs are reviewed.

The activity of allosteric modulators of mGluR2 in pain models has also been reported in the literature. See, Jones et al., Neuropharmacology. 2005; 49 Suppl 1:206-18, where analgesic effects of the selective group II (mGlu2/3) metabotropic glutamate receptor agonists are disclosed.

The efficacy of compounds of formula (I) of this invention in treating epilepsy can also be ascertained by various methods used in the art. For example, see, Alexander et al., Epilepsy Res. 2006, 71(1), 1-22, where metabotropic glutamate receptors as a strategic target for the treatment of epilepsy is discussed. Also see, Klodzinska et al., Pol J. Pharmacol. 1999, 51(6), 543-5, which discloses selective group II glutamate metabotropic receptor agonist LY354740 attenuates pentylenetetrazole- and picrotoxin-induced seizures. Roles of metabotropic glutamate receptor subtypes in modulation of pentylenetetrazole-induced seizure activity in mice is disclosed by Thomsen et al., Neuropharmacology. 1998, 37(12), 1465-73. Finally, Thomsen et al., J. Neurochem. 1994, 62(6), 2492-5, disclose that (S)-4-carboxy-3-hydroxyphenylglycine, an antagonist of metabotropic glutamate receptor (mGluR) 1a and an agonist of mGluR2, protects against audiogenic seizures in DBA/2 mice.

All of the references described herein are incorporated herein by reference in their entirety.

Example 4

Stress Induced Hyperthermia (Anxiety Model)

Stress-induced hyperthermia (SIH) reflects the elevation in core body temperature experienced by mammals following a stressful experience. Clinically active anxiolytics prevent SIH, indicating that this model may be useful in identifying novel anxiolytic agents (See, Olivier et al. Eur J. Pharmacol. 2003, 463, 117-32). SIH was measured in mice using the rectal test procedure adaptation of the classic SIH paradigm described by Borsini et al, Psychopharmacology (Berl). 1989, 98(2), 207-11. Individually housed mice were subjected to two sequential rectal temperature measurements, separated by a 10-minute interval. The first measurement captured the animal's basal core body temperature (T1), while the second temperature (T2) captured body temperature following the mild stress imposed by the first temperature measurement. The difference between the first and second temperature (T2−T1 or ΔT) is the SIH. Temperature measurements were made to the nearest 0.1° C. with a lubricated thermistor probe inserted 2 cm into the rectum of each subject. Test compounds were administered 60 minutes before the first temperature measurement to allow for any stress effect created by the injection to dissipate completely.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:
1. A compound of the formula I:

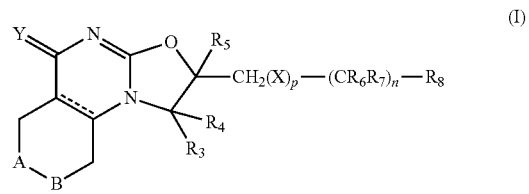

wherein:
- - - - - is a single or a double bond;
p is 0 or 1;
n is an integer from 0 to 3;
X is oxygen, sulfur or $NR_{21}$, wherein $R_{21}$ is hydrogen or $(C_1-C_4)$alkyl;
Y is oxygen or sulfur;
A is a single covalent bond or $CHR_1$;
B is $CHR_2$, $NR_2$, oxygen or sulfur;
$R_1$ and $R_2$ are the same or different and independently of each other selected from the group consisting of hydrogen, $CF_3$, straight or branched chain $(C_1-C_{10})$alkyl, mono- or di-fluoro$(C_1-C_4)$alkyl, mono- or di-fluoro$(C_1-C_4)$alkoxy$(C_0-C_4)$alkyl, mono- or di-fluoro$(C_1-C_4)$alkylsulfanyl$(C_0-C_4)$alkyl, mono- or di-fluoro$(C_1-C_4)$alkylsulfinyl$(C_0-C_4)$alkyl, mono- or di-fluoro$(C_1-C_4)$alkylsulfonyl$(C_0-C_4)$alkyl, $(C_1-C_{10})$alkoxy$(C_0-C_4)$alkyl, $(C_1-C_{10})$alkylsulfanyl$(C_0-C_4)$alkyl, $(C_1-C_{10})$alkylsulfinyl$(C_0-C_4)$alkyl, $(C_1-C_{10})$alkylsulfonyl$(C_0-C_4)$alkyl, $(C_1-C_{10})$alkoxy mono- or di-fluoro$(C_1-C_4)$alkyl, $(C_1-C_{10})$alkylsulfanyl mono- or di-fluoro$(C_1-C_4)$alkyl, $(C_1-C_{10})$alkylsulfinyl mono- or di-fiuoro$(C_1-C_4)$alkyl, $(C_1-C_{10})$alkylsulfonyl mono- or di-fluoro$(C_1-C_4)$alkyl, $(C_6,C_{10})$aryl$(C_0-C_4)$alkyl, $(C_6,C_{10})$aryl mono- or difluoro$(C_1-C_4)$alkyl, $(C_6,C_{10})$aryl mono- or difluoro $(C_2-C_4)$alkyloxy, $(C_6,C_{10})$aryloxy$(C_0-C_4)$alkyl, $(C_6,C_{10})$arylsulfanyl$(C_0-C_4)$alkyl, $(C_6,C_{10})$arylsulfinyl$(C_0-C_4)$alkyl, $(C_6,C_{10})$arylsulfonyl$(C_0-C_4)$alkyl, $(C_3-C_8)$cycloalkyl$(C_0-C_4)$alkyl, mono- or difluoro$(C_3-C_8)$cycloalkyl$(C_0-C_4)$alkyl, $(C_3-C_8)$cycloalkoxy$(C_0-C_4)$alkyl, mono- or difluoro$(C_3-C_8)$cycloalkyloxy$(C_0-C_4)$alkyl, $(C_3-C_8)$cycloalkyl mono- or difluoro$(C_1-C_4)$alkyl, $(C_3-C_8)$cycloalkyl mono- or difluoro $(C_2-C_4)$alkyloxy, $(C_3-C_8)$cycloalkylsulfanyl$(C_0-C_4)$alkyl, $(C_3-C_8)$cycloalkylsulfinyl$(C_0-C_4)$alkyl, $(C_3-C_8)$cycloalkylsulfonyl$(C_0-C_4)$alkyl, hydroxy$(C_1-C_4)$alkyl, heteroaryl$(C_0-C_4)$alkyl, heteroaryl mono- or difluoro $(C_1-C_4)$alkyl, heteroaryloxy$(C_0-C_4)$alkyl, heteroaryloxy mono- or difluoro$(C_2-C_4)$alkyl, heteroarylsulfanyl$(C_0-C_4)$alkyl, heteroarylsulfinyl$(C_0-C_4)$alkyl, heteroarylsulfonyl$(C_0-C_4)$alkyl, saturated heterocyclic $(C_0-C_4)$alkyl, saturated heterocyclic mono- or di-fluoro $(C_1-C_4)$alkyl, saturated heterocyclyloxy$(C_0-C_4)$alkyl, saturated heterocyclyloxy mono- or di-fluoro($C_2$-$C_4$) alkyl, saturated heterocyclylsulfanyl($C_0$-$C_4$)alkyl, heterocyclylsulfinyl($C_0$-$C_4$)alkyl, heterocyclylsulfonyl ($C_0$-$C_4$)alkyl, —$CO_2R_{22}$ or —$CONR_{23}R_{24}$ wherein $R_{22}$, $R_{23}$ and $R_{24}$ are the same or different and independently of each other selected from hydrogen or ($C_1$-$C_4$)alkyl; and wherein $R_1$ and $R_2$ are optionally further substituted;

$R_3$ and $R_4$ are the same or different and independently of each other selected from the group consisting of hydrogen, ($C_1$-$C_4$)alkyl, ($C_3$-$C_8$)cycloalkyl and ($C_6$,$C_{10}$)aryl ($C_1$-$C_4$)alkyl; or $R_3$ and $R_4$ taken together with the carbon atom to which they are attached form a substituted or unsubstituted $C_5$-$C_7$ carbocyclic ring;

$R_5$, $R_6$ and $R_7$ are the same or different and independently of each other selected from the group consisting of hydrogen, ($C_1$-$C_4$)alkyl and ($C_3$-$C_8$)cycloalkyl;

$R_8$ is selected from the group consisting of substituted phenyl, substituted or unsubstituted naphthyl, substituted or unsubstituted indanyl, substituted or unsubstituted tetralinyl, substituted or unsubstituted benzocycloheptanyl, substituted or unsubstituted hexahydrofluorenyl, substituted or unsubstituted ($C_3$-$C_8$)cycloalkyl, substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, substituted or unsubstituted tetrahydrodibenzofuranyl and substituted or unsubstituted hexahydrodibenzofuranyl;

wherein said substituents are selected from the group consisting of $CF_3$, $OCF_3$, halogen, CN, $SF_5$, ($C_1$-$C_4$) alkylsulfonyl, substituted or unsubstituted ($C_3$-$C_{10}$)cycloalkyl($CR_9R_{10}$)$_m$, substituted or unsubstituted ($C_6$-$C_{16}$)spirocycloalkyl, substituted or unsubstituted ($C_6$,$C_{10}$)aryl($CR_9R_{10}$)$_m$, substituted or unsubstituted heteroaryl($CR_9R_{10}$)$_m$, substituted or unsubstituted ($C_6$,$C_{10}$)aryl($C_3$-$C_8$)cycloalkyl, substituted or unsubstituted ($C_8$-$C_{13}$)bicyclic, substituted or unsubstituted adamantyl, substituted or unsubstituted indanyl, substituted or unsubstituted tetralinyl, substituted or unsubstituted benzocycloheptyl, straight or branched chain ($C_1$-$C_{20}$) alkoxy, substituted or unsubstituted ($C_3$-$C_{10}$)cycloalkoxy, substituted or unsubstituted ($C_6$,$C_{10}$)aryloxy, substituted or unsubstituted heteroaryloxy, substituted or unsubstituted piperidinyl($CR_9R_{10}$)$_m$, substituted or unsubstituted piperazinyl($CR_9R_{10}$)$_m$, substituted or unsubstituted ($C_4$-$C_7$)lactam, substituted or unsubstituted tetrahydropyranyl($CR_9R_{10}$)$_m$, substituted or unsubstituted tetrahydrofuranyl($CR_9R_{10}$)$_m$, substituted or unsubstituted 1,3-dioxanyl, substituted or unsubstituted 1,3-dioxolanyl, ($C_1$-$C_4$)alkoxyethoxy, substituted or unsubstituted ($C_3$-$C_8$)cycloalkyloxyethoxy, substituted or unsubstituted ($C_6$,$C_{10}$)aryloxyethoxy and substituted or unsubstituted heteroaryloxyethoxy; wherein m is an integer from 0 to 10;

$R_9$ and $R_{10}$ are the same or different and independently of each other chosen from hydrogen or ($C_1$-$C_4$)alkyl; or $R_9$ and $R_{10}$ taken together with the carbon atom to which they are attached form a substituted or unsubstituted $C_3$-$C_8$ carbocyclic ring;

and wherein said substituents are selected from the aforementioned substituents;

or a salt thereof or an enantiomer, stereoisomer or a tautomer thereof or a racemic mixture thereof.

2. The compound according to claim 1, wherein ----- is a double bond;

p is 1;

n is 0;

X and Y are oxygen;

A is a single covalent bond or $CHR_1$;

B is $CHR_2$ or $NR_2$;

$R_1$ and $R_2$ are the same or different and independently of each other selected from hydrogen, $CF_3$, straight or branched ($C_1$-$C_{10}$)alkyl, mono- or di-fluoro($C_1$-$C_4$) alkyl, mono- or di-fluoro($C_1$-$C_4$)alkoxy($C_0$-$C_4$alkyl, ($C_1$-$C_{10}$)alkoxy($C_0$-$C_4$)alkyl, ($C_6$,$C_{10}$)aryl, ($C_6$,$C_{10}$) aryl($C_1$-$C_4$)alkyl ($C_3$-$C_8$)cycloalkyl($C_0$-$C_4$)alkyl, ($C_3$-$C_8$)cycloalkoxy($C_0$-$C_4$)alkyl, hydroxy($C_1$-$C_4$)alkyl or -$CO_2C_2H_5$;

$R_3$, $R_4$ and $R_5$ are hydrogen;

$R_8$ is selected from the group consisting of substituted phenyl, substituted or unsubstituted indanyl, substituted or unsubstituted tetralinyl, substituted or unsubstituted benzocycloheptanyl, substituted or unsubstituted hexahydrofluorenyl and substituted or unsubstituted cyclohexyl; wherein said substituents are selected from the group consisting of $CF_3$, $OCF_3$, $SF_5$, fluorine, chlorine, bromine, CN, substituted or unsubstituted ($C_3$-$C_{10}$) cycloalkyl($CR_9R_{10}$)$_m$, unsubstituted ($C_6$,$C_{10}$)aryl ($CR_9R_{10}$)$_m$, substituted or unsubstituted ($C_6$,$C_{10}$)aryl ($C_3$-$C_8$)cycloalkyl, substituted or unsubstituted ($C_8$-$C_{13}$)bicyclic, substituted or unsubstituted adamantyl, substituted or unsubstituted indanyl, substituted or unsubstituted tetralinyl, substituted or unsubstituted benzocycloheptyl, straight or branched chain ($C_1$-$C_{20}$) alkoxy, substituted or unsubstituted ($C_3$-$C_{10}$)cycloalkoxy, substituted or unsubstituted ($C_6$,$C_{10}$)aryloxy, substituted or unsubstituted heteroaryloxy and substituted or unsubstituted tetrahydropyranyl($CR_9R_{10}$)$_m$; wherein m is an integer from 0 to 2;

$R_9$ and $R_{10}$ are the same or different and independently of each other chosen from hydrogen or ($C_1$-$C_4$)alkyl; or $R_9$ and $R_{10}$ taken together with the carbon atom to which they are attached form a substituted or unsubstituted $C_3$-$C_8$ ring;

and wherein said substituents are selected from the aforementioned substituents;

or a salt thereof or an enantiomer, stereoisomer or a tautomer thereof or a racemic mixture thereof.

3. The compound according to claim 1, having the formula II:

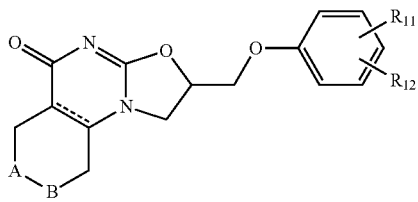

wherein:
----- is a single or a double bond;
A is a single covalent bond;
B is $CHR_2$ or $NR_2$;
$R_1$ and $R_2$ are the same or different and independently of each other selected from hydrogen, $CF_3$, straight or branched $(C_1-C_{10})$alkyl, mono- or di-fluoro$(C_1-C_4)$alkyl, mono- or di-fluoro$(C_1-C_4)$alkoxy$(C_0-C_4)$alkyl, $(C_1-C_{10})$alkoxy$(C_0-C_4)$alkyl, $(C_6,C_{10})$aryl, $(C_6,C_{10})$aryl$(C_1-C_4)$alkyl, phenylsulfanyl$(C_0-C_4)$alkyl, phenylsulfinyl$(C_0-C_4)$alkyl, phenylsulfonyl$(C_0-C_4)$alkyl, $(C_3-C_8)$cycloalkyl$(C_0-C_4)$alkyl, $(C_3-C_8)$cycloalkoxy$(C_0-C_4)$alkyl, hydroxy$(C_1-C_4)$alkyl or $—CO_2C_2H_5$;
$R_{11}$ and $R_{12}$ are the same or different and independently of each other selected from the group consisting of hydrogen, $CF_3$, $OCF_3$, $SF_5$, fluorine, chlorine, bromine, CN, substituted or unsubstituted $(C_3-C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_3-C_{10})$cycloalkoxy, substituted or unsubstituted tetrahydropyranyl$(CR_9R_{10})_m$, substituted or unsubstituted $(C_6,C_{10})$aryloxy and substituted or unsubstituted heteroaryloxy; wherein one of $R_{11}$ and $R_{12}$ is other than hydrogen; and wherein
m is 0 or 1;
$R_9$ and $R_{10}$ are the same or different and independently of each other chosen from hydrogen or $(C_1-C_4)$alkyl;
and wherein said substituents are selected from the group consisting of halogen, straight or branched chain $C_1-C_{10}$alkyl, phenyl, indanyl and imidazolyl;
or a salt thereof or an enantiomer, stereoisomer or a tautomer thereof or a racemic mixture thereof.

4. The compound according to claim 3, which is:
2-(4-cyclohexyl-phenoxymethyl)-1,2,7,8-tetrahydro-6H-3-oxa-4,8b-diaza-as-indacen-5-one;
or a salt thereof.

5. A compound having the formula II:

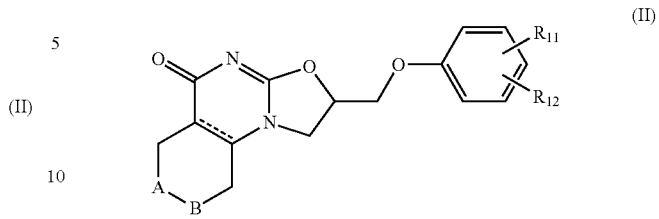

wherein:
----- is a single or a double bond;
A is $CHR_1$;
B is $CHR_2$ or $NR_2$;
$R_1$ and $R_2$ are the same or different and independently of each other selected from hydrogen, $CF_3$, straight or branched $(C_1-C_{10})$alkyl, mono- or di-fluoro$(C_1-C_4)$alkyl, mono- or di-fluoro$(C_1-C_4)$alkoxy$(C_0-C_4)$alkyl, $(C_1-C_{10})$alkoxy$(C_0-C_4)$alkyl, $(C_6,C_{10})$aryl, $(C_6,C_{10})$aryl$(C_1-C_4)$alkyl, phenylsulfanyl$(C_0-C_4)$alkyl, phenylsulfinyl$(C_0-C_4)$alkyl, phenylsulfonyl$(C_0-C_4)$alkyl, $(C_3-C_8)$cycloalkyl$(C_0-C_4)$alkyl, $(C_3-C_8)$cycloalkoxy$(C_0-C_4)$alkyl, hydroxy$(C_1-C_4)$alkyl or $—CO_2C_2H_5$;
$R_{11}$ and $R_{12}$ are the same or different and independently of each other selected from the group consisting of $CF_3$, $OCF_3$, $SF_5$, fluorine, chlorine, bromine, CN, straight or branched chain $(C_1-C_{20})$alkyl, substituted or unsubstituted $(C_3-C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_3-C_{10})$cycloalkoxy, substituted or unsubstituted tetrahydropyranyl$(CR_9R_{10})_m$, substituted or unsubstituted $(C_6,C_{10})$aryloxy and substituted or unsubstituted heteroaryloxy; and wherein
m is 0 or 1;
$R_9$ and $R_{10}$ are the same or different and independently of each other chosen from hydrogen or $(C_1-C_4)$alkyl;
and wherein said substituents are selected from the group consisting of halogen,
straight or branched chain $C_1-C_{10}$alkyl, phenyl, indanyl and imidazolyl;
or a salt thereof or an enantiomer, stereoisomer or a tautomer thereof or a racemic mixture thereof.

6. The compound according to claim 1, which is:
2-(4-cyclohexyl-phenoxymethyl)-1,2,6,7,8,9-hexahydro-oxazolo[3,2-a] quinazolin-5-one;
or a salt thereof.

7. A pharmaceutical composition comprising one or more compounds according to claim 1 or a pharmaceutically acceptable salt, an enantiomer, a stereoisomer or a tautomer thereof or a racemic mixture thereof, in combination with one or more pharmaceutically acceptable carriers, diluents or excipients.

8. A pharmaceutical composition comprising one or more compounds according to claim 2 or a pharmaceutically acceptable salt, an enantiomer, a stereoisomer or a tautomer thereof or a racemic mixture thereof, in combination with one or more pharmaceutically acceptable carriers, diluents or excipients.

9. A pharmaceutical composition comprising one or more compounds according to claim 3 or a pharmaceutically acceptable salt, an enantiomer, a stereoisomer or a tautomer thereof or a racemic mixture thereof, in combination with one or more pharmaceutically acceptable carriers, diluents or excipients.

10. A pharmaceutical composition comprising one or more compounds according to claim 4 or a pharmaceutically acceptable salt, an enantiomer, a stereoisomer or a tautomer thereof or a racemic mixture thereof, in combination with one or more pharmaceutically acceptable carriers, diluents or excipients.

11. A pharmaceutical composition comprising one or more compounds according to claim 5 or a pharmaceutically acceptable salt, an enantiomer, a stereoisomer or a tautomer thereof or a racemic mixture thereof, in combination with one or more pharmaceutically acceptable carriers, diluents or excipients.

12. A pharmaceutical composition comprising one or more compounds according to claim 6 or a pharmaceutically acceptable salt, an enantiomer, a stereoisomer or a tautomer thereof or a racemic mixture thereof, in combination with one or more pharmaceutically acceptable carriers, diluents or excipients.

13. A method of modulating one or more metabotropic glutamate receptors, comprising administering an effective amount of a compound according to claim 1 or a pharmaceutically acceptable salt, an enantiomer, a stereoisomer or a tautomer thereof or a racemic mixture thereof.

\* \* \* \* \*

UNITED STATES PATENT AND TRADEMARK OFFICE
CERTIFICATE OF CORRECTION

PATENT NO. : 8,207,181 B2
APPLICATION NO. : 12/875700
DATED : June 26, 2012
INVENTOR(S) : Raymond Walter Kosley, Jr. et al.

It is certified that error appears in the above-identified patent and that said Letters Patent is hereby corrected as shown below:

On the Title page, in field (56), in column 2, under "Other Publications", line 7, delete "Archie" and insert -- Archiv --, therefor.

In column 16, line 59, delete "(VIIIe)." and insert -- (VIIIc). --, therefor.

In column 24, line 46, in claim 1, delete "di-fiuoro($C_1$-$C_4$)" and insert -- di-fluoro($C_1$-$C_4$) --, therefor.

In column 26, line 25, in claim 2, delete "($C_0$-$C_4$alkyl," and insert -- ($C_0$-$C_4$)alkyl, --, therefor.

In column 26, line 42, in claim 2, after "$(CR_9R_{10})_m$," insert -- substituted or --.

Signed and Sealed this
Thirtieth Day of October, 2012

David J. Kappos
*Director of the United States Patent and Trademark Office*